United States Patent
Barak et al.

(10) Patent No.: US 11,712,213 B2
(45) Date of Patent: *Aug. 1, 2023

(54) SYSTEM AND METHOD FOR POSE ESTIMATION OF AN IMAGING DEVICE AND FOR DETERMINING THE LOCATION OF A MEDICAL DEVICE WITH RESPECT TO A TARGET

(71) Applicant: Covidien LP, Mansfield, MA (US)

(72) Inventors: Ron Barak, Tel Aviv (IL); Ariel Birenbaum, Raanana (IL); Guy Alexandroni, Haifa (IL); Oren P. Weingarten, Hod-Hasharon (IL)

(73) Assignee: COVIDIEN LP, Mansfield, MA (US)

( * ) Notice: Subject to any disclaimer, the term of this patent is extended or adjusted under 35 U.S.C. 154(b) by 270 days.

This patent is subject to a terminal disclaimer.

(21) Appl. No.: 17/142,642

(22) Filed: Jan. 6, 2021

(65) Prior Publication Data
US 2021/0145387 A1 May 20, 2021

Related U.S. Application Data

(63) Continuation of application No. 16/270,246, filed on Feb. 7, 2019, now Pat. No. 10,893,842.
(Continued)

(51) Int. Cl.
*G06T 7/73* (2017.01)
*G06T 7/77* (2017.01)
(Continued)

(52) U.S. Cl.
CPC .......... *A61B 6/487* (2013.01); *A61B 1/00158* (2013.01); *A61B 1/043* (2013.01);
(Continued)

(58) Field of Classification Search
CPC ..... A61B 6/487; A61B 1/00158; A61B 1/043; A61B 5/055; A61B 5/064; A61B 34/20; A61B 90/36; A61B 90/39; A61B 1/0005; A61B 1/042; A61B 6/032; A61B 2034/2051; A61B 2034/2055;
(Continued)

(56) References Cited

U.S. PATENT DOCUMENTS

| 5,023,895 A | 6/1991 | Mccroskey et al. |
| 5,057,494 A | 10/1991 | Sheffield |

(Continued)

FOREIGN PATENT DOCUMENTS

| BR | 0013237 A | 7/2003 |
| BR | 0116004 A | 6/2004 |

(Continued)

OTHER PUBLICATIONS

International Search Report and Written Opinion of the International Searching Authority issued in corresponding Appl. No. PCT/US2019/017231 dated May 30, 2019 (12 pages).

(Continued)

*Primary Examiner* — Jon Chang
(74) *Attorney, Agent, or Firm* — Weber Rosselli & Cannon LLP

(57) ABSTRACT

A system and method for estimating a pose of an imaging device for one or more images is provided.

20 Claims, 10 Drawing Sheets

Related U.S. Application Data

(60) Provisional application No. 62/641,777, filed on Mar. 12, 2018, provisional application No. 62/628,017, filed on Feb. 8, 2018.

(51) Int. Cl.
  G06T 7/70 (2017.01)
  A61B 6/00 (2006.01)
  A61B 5/055 (2006.01)
  A61B 34/20 (2016.01)
  A61B 1/04 (2006.01)
  A61B 1/00 (2006.01)
  A61B 90/00 (2016.01)
  A61B 5/06 (2006.01)
  A61B 6/03 (2006.01)

(52) U.S. Cl.
  CPC ............ *A61B 5/055* (2013.01); *A61B 5/064* (2013.01); *A61B 34/20* (2016.02); *A61B 90/36* (2016.02); *A61B 90/39* (2016.02); *G06T 7/70* (2017.01); *G06T 7/73* (2017.01); *G06T 7/75* (2017.01); *G06T 7/77* (2017.01); *A61B 1/0005* (2013.01); *A61B 1/042* (2013.01); *A61B 6/032* (2013.01); *A61B 2034/2051* (2016.02); *A61B 2034/2055* (2016.02); *A61B 2090/364* (2016.02); *A61B 2090/3983* (2016.02); *G06T 2207/10016* (2013.01); *G06T 2207/10068* (2013.01); *G06T 2207/10081* (2013.01); *G06T 2207/10088* (2013.01); *G06T 2207/10121* (2013.01); *G06T 2207/30021* (2013.01); *G06T 2207/30208* (2013.01); *G06T 2207/30244* (2013.01)

(58) Field of Classification Search
  CPC ...... A61B 2090/364; A61B 2090/3983; G06T 7/70; G06T 7/73; G06T 7/75; G06T 7/77; G06T 2207/10016; G06T 2207/10068; G06T 2207/10081; G06T 2207/10088; G06T 2207/10121; G06T 2207/30021; G06T 2207/30208; G06T 2207/30244; G06T 7/30; G06T 7/0012; G06T 2207/30004; G06T 2207/30061; G06T 2207/30096; G06T 7/248; G06T 7/251; G06T 7/269
  See application file for complete search history.

(56) References Cited

U.S. PATENT DOCUMENTS

| | | | |
|---|---|---|---|
| 5,321,113 A | 6/1994 | Cooper et al. | |
| 5,488,952 A | 2/1996 | Schoolman | |
| 5,493,595 A | 2/1996 | Schoolman | |
| 5,668,846 A | 9/1997 | Fox et al. | |
| 6,003,517 A | 12/1999 | Sheffield et al. | |
| 6,101,234 A | 8/2000 | Ali et al. | |
| 6,201,849 B1 | 3/2001 | Lai | |
| 6,206,566 B1 | 3/2001 | Schuetz | |
| 6,289,235 B1 | 9/2001 | Webber et al. | |
| 6,317,621 B1 | 11/2001 | Graumann et al. | |
| 6,359,960 B1 | 3/2002 | Wahl et al. | |
| 6,370,224 B1 | 4/2002 | Simon et al. | |
| 6,373,916 B1 | 4/2002 | Inoue et al. | |
| 6,379,041 B1 | 4/2002 | Schuetz et al. | |
| 6,382,835 B2 | 5/2002 | Graumann et al. | |
| 6,404,843 B1 | 6/2002 | Vaillant | |
| 6,442,288 B1 | 8/2002 | Haerer et al. | |
| 6,463,116 B1 | 10/2002 | Oikawa | |
| 6,466,638 B1 | 10/2002 | Silver et al. | |
| 6,470,207 B1 | 10/2002 | Simon et al. | |
| 6,473,634 B1 | 10/2002 | Barni | |
| 6,484,049 B1 | 11/2002 | Seeley et al. | |
| 6,490,475 B1 | 12/2002 | Seeley et al. | |
| 6,504,892 B1 | 1/2003 | Ning | |
| 6,519,355 B2 | 2/2003 | Nelson | |
| 6,522,712 B1 | 2/2003 | Yavuz et al. | |
| 6,587,539 B2 | 7/2003 | Oikawa | |
| 6,636,623 B2 | 10/2003 | Nelson et al. | |
| 6,643,351 B2 | 11/2003 | Morita et al. | |
| 6,666,579 B2 | 12/2003 | Jensen | |
| 6,697,664 B2 | 2/2004 | Kienzle et al. | |
| 6,707,878 B2 | 3/2004 | Claus et al. | |
| 6,735,914 B2 | 5/2004 | Konopka | |
| 6,751,284 B1 | 6/2004 | Claus et al. | |
| 6,782,287 B2 | 8/2004 | Grzeszczuk et al. | |
| 6,787,750 B1 * | 9/2004 | Sauer ...................... G06T 7/73 | 250/559.4 |
| 6,810,278 B2 | 10/2004 | Webber et al. | |
| 6,823,207 B1 | 11/2004 | Jensen et al. | |
| 6,834,096 B2 | 12/2004 | Launay et al. | |
| 6,837,892 B2 | 1/2005 | Shoham | |
| 6,851,855 B2 | 2/2005 | Mitschke et al. | |
| 6,856,826 B2 | 2/2005 | Seeley et al. | |
| 6,856,827 B2 | 2/2005 | Seeley et al. | |
| 6,904,121 B2 | 6/2005 | Claus et al. | |
| 6,909,794 B2 | 6/2005 | Caspi | |
| 6,912,265 B2 | 6/2005 | Hebecker et al. | |
| 6,980,624 B2 | 12/2005 | Li et al. | |
| 6,987,829 B2 | 1/2006 | Claus | |
| 7,048,440 B2 | 5/2006 | Graumann et al. | |
| 7,082,181 B2 | 7/2006 | Nishide et al. | |
| 7,085,345 B2 | 8/2006 | Nukui | |
| 7,103,136 B2 | 9/2006 | Claus et al. | |
| 7,120,283 B2 | 10/2006 | Thieret et al. | |
| 7,123,682 B2 | 10/2006 | Kotian et al. | |
| 7,142,633 B2 | 11/2006 | Eberhard et al. | |
| 7,187,792 B2 | 3/2007 | Fu et al. | |
| 7,197,107 B2 | 3/2007 | Arai et al. | |
| 7,251,522 B2 | 7/2007 | Essenreiter et al. | |
| 7,310,436 B2 | 12/2007 | Li et al. | |
| 7,327,865 B2 | 2/2008 | Fu et al. | |
| 7,327,872 B2 | 2/2008 | Vaillant et al. | |
| 7,369,695 B2 | 5/2008 | Zettel et al. | |
| 7,371,067 B2 | 5/2008 | Anderson et al. | |
| 7,376,213 B1 | 5/2008 | Wei et al. | |
| 7,398,116 B2 | 7/2008 | Edwards | |
| 7,447,295 B2 | 11/2008 | Hoheisel et al. | |
| 7,457,451 B2 | 11/2008 | Hsieh et al. | |
| 7,499,743 B2 | 3/2009 | Vass et al. | |
| 7,519,414 B2 | 4/2009 | Mitschke et al. | |
| 7,519,415 B2 | 4/2009 | Mitschke et al. | |
| 7,522,755 B2 | 4/2009 | Avinash et al. | |
| 7,551,759 B2 | 6/2009 | Hristov et al. | |
| 7,558,366 B2 | 7/2009 | Barth et al. | |
| 7,568,837 B2 | 8/2009 | Heigl et al. | |
| 7,603,155 B2 | 10/2009 | Jensen et al. | |
| 7,620,444 B2 | 11/2009 | Le et al. | |
| 7,633,501 B2 | 12/2009 | Wood et al. | |
| 7,683,338 B2 | 3/2010 | Ueno et al. | |
| 7,693,254 B2 | 4/2010 | Muller et al. | |
| 7,693,318 B1 | 4/2010 | Stalling et al. | |
| 7,711,409 B2 | 5/2010 | Keppel et al. | |
| 7,712,961 B2 | 5/2010 | Horndler et al. | |
| 7,742,557 B2 | 6/2010 | Brunner et al. | |
| 7,744,279 B2 | 6/2010 | Heath et al. | |
| 7,756,244 B2 | 7/2010 | Mostafavi | |
| 7,761,136 B2 | 7/2010 | Ohishi et al. | |
| 7,778,690 B2 | 8/2010 | Boese et al. | |
| 7,801,587 B2 | 9/2010 | Webber et al. | |
| 7,813,469 B2 | 10/2010 | Siltanen et al. | |
| 7,826,884 B2 | 11/2010 | Baumgart | |
| 7,831,013 B2 | 11/2010 | Star-Lack et al. | |
| 7,835,491 B2 | 11/2010 | Fischer et al. | |
| 7,840,093 B2 | 11/2010 | Fu et al. | |
| 7,844,094 B2 | 11/2010 | Jeung et al. | |
| 7,853,061 B2 | 12/2010 | Gorges et al. | |
| 7,873,236 B2 | 1/2011 | Li et al. | |
| 7,877,132 B2 | 1/2011 | Rongen et al. | |
| 7,899,226 B2 | 3/2011 | Pescatore et al. | |
| 7,912,180 B2 | 3/2011 | Zou et al. | |

(56) References Cited

U.S. PATENT DOCUMENTS

| | | |
|---|---|---|
| 7,916,918 B2 | 3/2011 | Suri et al. |
| 7,920,909 B2 | 4/2011 | Lyon et al. |
| 7,940,885 B2 | 5/2011 | Stanton et al. |
| 7,974,450 B2 | 7/2011 | Ritter et al. |
| 7,978,886 B2 | 7/2011 | Claus et al. |
| 7,986,762 B2 | 7/2011 | Kunze |
| 7,995,819 B2 | 8/2011 | Vaillant et al. |
| 8,045,780 B2 | 10/2011 | Boese et al. |
| 8,050,739 B2 | 11/2011 | Eck et al. |
| 8,107,592 B2 | 1/2012 | Berman et al. |
| 8,126,224 B2 | 2/2012 | Zuhars et al. |
| 8,150,131 B2 | 4/2012 | Harer et al. |
| 8,180,132 B2 | 5/2012 | Gorges et al. |
| 8,213,564 B2 | 7/2012 | Dennerlein et al. |
| 8,229,061 B2 | 7/2012 | Hanke et al. |
| 8,233,962 B2 | 7/2012 | Kukuk et al. |
| 8,275,445 B2 | 9/2012 | Berting |
| 8,326,403 B2 | 12/2012 | Pescatore et al. |
| 8,335,359 B2 | 12/2012 | Fidrich et al. |
| 8,411,923 B2 | 4/2013 | Ludwig et al. |
| 8,447,009 B2 | 5/2013 | Flohr et al. |
| 8,482,606 B2 | 7/2013 | Razzaque et al. |
| 8,483,358 B2 | 7/2013 | Allison |
| 8,526,688 B2 | 9/2013 | Groszmann et al. |
| 8,542,900 B2 | 9/2013 | Tolkowsky et al. |
| 8,554,307 B2 | 10/2013 | Razzaque et al. |
| 8,565,502 B2 | 10/2013 | Zeng et al. |
| 8,600,138 B2 | 12/2013 | Gorges et al. |
| 8,625,869 B2 | 1/2014 | Harder et al. |
| 8,644,595 B2 | 2/2014 | Stanton et al. |
| 8,675,996 B2 | 3/2014 | Liao et al. |
| 8,693,756 B2 | 4/2014 | Tolkowsky et al. |
| 8,694,075 B2 | 4/2014 | Groszmann et al. |
| 8,699,670 B2 | 4/2014 | Graumann et al. |
| 8,706,184 B2 | 4/2014 | Mohr et al. |
| 8,750,582 B2 | 6/2014 | Boese et al. |
| 8,774,355 B2 | 7/2014 | Claus et al. |
| 8,798,348 B2 | 8/2014 | Muller et al. |
| 8,798,353 B2 | 8/2014 | Claus |
| 8,824,765 B2 | 9/2014 | Dennerlein |
| 8,827,934 B2 | 9/2014 | Chopra et al. |
| 8,831,169 B2 | 9/2014 | Zaiki et al. |
| 8,923,476 B2 | 12/2014 | Paidi et al. |
| 8,989,342 B2 | 3/2015 | Liesenfelt et al. |
| 9,001,963 B2 | 4/2015 | Sowards-Emmerd et al. |
| 9,026,217 B2 | 5/2015 | Kokones et al. |
| 9,042,624 B2 | 5/2015 | Dennerlein |
| 9,044,190 B2 | 6/2015 | Rubner et al. |
| 9,095,306 B2 | 8/2015 | Gkanatsios et al. |
| 9,104,902 B2 | 8/2015 | Xu et al. |
| 9,349,198 B2 | 5/2016 | Claus et al. |
| 9,375,268 B2 | 6/2016 | Long |
| 9,380,985 B2 | 7/2016 | Akahori |
| 9,401,047 B2 | 7/2016 | Bogoni et al. |
| 9,433,390 B2 | 9/2016 | Nathaniel et al. |
| 9,454,813 B2 | 9/2016 | Westerhoff et al. |
| 9,460,512 B2 | 10/2016 | Ohishi et al. |
| 9,466,135 B2 | 10/2016 | Koehler et al. |
| 9,743,896 B2 | 8/2017 | Averbuch |
| 9,833,167 B2 | 12/2017 | Cohen et al. |
| 9,888,898 B2 | 2/2018 | Imagawa et al. |
| 9,918,659 B2 | 3/2018 | Chopra et al. |
| 10,004,558 B2 | 6/2018 | Long |
| 10,127,629 B2 | 11/2018 | Razzaque et al. |
| 10,130,316 B2 | 11/2018 | Funabasama et al. |
| 10,194,897 B2 | 2/2019 | Cedro et al. |
| 10,373,719 B2 | 8/2019 | Soper et al. |
| 10,376,178 B2 | 8/2019 | Chopra |
| 10,405,753 B2 | 9/2019 | Sorger |
| 10,478,162 B2 | 11/2019 | Barbagli et al. |
| 10,480,926 B2 | 11/2019 | Froggatt et al. |
| 10,524,866 B2 | 1/2020 | Srinivasan et al. |
| 10,555,788 B2 | 2/2020 | Panescu et al. |
| 10,569,071 B2 | 2/2020 | Harris et al. |
| 10,603,106 B2 | 3/2020 | Weide et al. |
| 10,610,306 B2 | 4/2020 | Chopra |
| 10,638,953 B2 | 5/2020 | Duindam et al. |
| 10,639,114 B2 | 5/2020 | Schuh et al. |
| 10,674,970 B2 | 6/2020 | Averbuch et al. |
| 10,682,070 B2 | 6/2020 | Duindam |
| 10,702,137 B2 | 7/2020 | Deyanov |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,885,630 B2 | 1/2021 | Li et al. |
| 10,893,842 B2 * | 1/2021 | Barak .................. A61B 34/20 |
| 2001/0024291 A1 | 9/2001 | Selifonov et al. |
| 2002/0147462 A1 | 10/2002 | Mair et al. |
| 2003/0013972 A1 | 1/2003 | Makin |
| 2003/0031291 A1 | 2/2003 | Yamamoto et al. |
| 2003/0128801 A1 | 7/2003 | Eisenberg et al. |
| 2003/0130576 A1 | 7/2003 | Seeley et al. |
| 2003/0181809 A1 | 9/2003 | Hall et al. |
| 2003/0190065 A1 | 10/2003 | Hamill et al. |
| 2004/0030585 A1 | 2/2004 | Sariel |
| 2004/0120981 A1 | 6/2004 | Nathan |
| 2005/0059879 A1 | 3/2005 | Sutherland et al. |
| 2005/0178970 A1 | 8/2005 | Amemiya et al. |
| 2005/0281385 A1 | 12/2005 | Johnson et al. |
| 2006/0142984 A1 | 6/2006 | Weese et al. |
| 2007/0030947 A1 | 2/2007 | Popescu |
| 2008/0045938 A1 | 2/2008 | Weide et al. |
| 2011/0152676 A1 | 6/2011 | Groszmann et al. |
| 2012/0046521 A1 | 2/2012 | Hunter et al. |
| 2012/0289825 A1 | 11/2012 | Rai et al. |
| 2013/0303945 A1 | 11/2013 | Blumenkranz et al. |
| 2014/0035798 A1 | 2/2014 | Kawada et al. |
| 2014/0221819 A1 | 8/2014 | Sarment |
| 2015/0148690 A1 | 5/2015 | Chopra et al. |
| 2015/0265368 A1 | 9/2015 | Chopra et al. |
| 2015/0288951 A1 * | 10/2015 | Mallet .................. G06T 7/80 348/46 |
| 2016/0005168 A1 | 1/2016 | Merlet et al. |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0287344 A1 | 10/2016 | Donhowe et al. |
| 2017/0112571 A1 | 4/2017 | Thiel et al. |
| 2017/0112576 A1 | 4/2017 | Coste-Maniere et al. |
| 2017/0209071 A1 | 7/2017 | Zhao et al. |
| 2017/0236285 A1 * | 8/2017 | Houri .................. G06V 30/422 382/103 |
| 2017/0265952 A1 | 9/2017 | Donhowe et al. |
| 2017/0311844 A1 | 11/2017 | Zhao et al. |
| 2017/0319165 A1 | 11/2017 | Averbuch |
| 2018/0078318 A1 | 3/2018 | Barbagli |
| 2018/0144092 A1 | 5/2018 | Flitsch et al. |
| 2018/0153621 A1 | 6/2018 | Duindam et al. |
| 2018/0160990 A1 | 6/2018 | Weingarten et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2019/0000559 A1 | 1/2019 | Berman et al. |
| 2019/0000560 A1 | 1/2019 | Berman et al. |
| 2019/0005687 A1 | 1/2019 | Weingarten et al. |
| 2019/0008413 A1 | 1/2019 | Duindam et al. |
| 2019/0038365 A1 | 2/2019 | Soper et al. |
| 2019/0046232 A1 | 2/2019 | Tokuda et al. |
| 2019/0065209 A1 | 2/2019 | Mishra et al. |
| 2019/0110839 A1 | 4/2019 | Rafii-Tari et al. |
| 2019/0175062 A1 | 6/2019 | Rafii-Tari et al. |
| 2019/0175799 A1 | 6/2019 | Hsu et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |

(56) References Cited

U.S. PATENT DOCUMENTS

| | | |
|---|---|---|
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0269818 A1 | 9/2019 | Dhanaraj et al. |
| 2019/0269819 A1 | 9/2019 | Dhanaraj et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0030044 A1 | 1/2020 | Wang et al. |
| 2020/0030461 A1 | 1/2020 | Sorger |
| 2020/0037928 A1 * | 2/2020 | Edwards ............... A61B 90/18 |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0054408 A1 | 2/2020 | Schuh et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078023 A1 | 3/2020 | Cedro et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138514 A1 | 5/2020 | Blumenkranz et al. |
| 2020/0138515 A1 | 5/2020 | Wong |
| 2020/0142013 A1 | 5/2020 | Wong |
| 2020/0155116 A1 | 5/2020 | Donhowe et al. |
| 2020/0155232 A1 | 5/2020 | Wong |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188021 A1 | 6/2020 | Wong et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |
| 2020/0383750 A1 | 12/2020 | Kemp et al. |
| 2021/0000524 A1 | 1/2021 | Barry et al. |

FOREIGN PATENT DOCUMENTS

| | | | |
|---|---|---|---|
| BR | 0307259 A | 12/2004 | |
| BR | 0412298 A2 | 9/2006 | |
| BR | 112018003862 A2 | 10/2018 | |
| CZ | 1644519 | 12/2008 | |
| CZ | 486540 | 9/2016 | |
| CZ | 2709512 | 8/2017 | |
| CZ | 2884879 | 1/2020 | |
| EP | 0846275 A1 | 6/1998 | |
| EP | 1326531 A2 | 7/2003 | |
| EP | 1644519 B1 | 12/2008 | |
| EP | 2141497 A1 | 1/2010 | |
| EP | 3413830 A4 | 9/2019 | |
| EP | 3478161 A4 | 2/2020 | |
| EP | 3641686 A2 | 4/2020 | |
| EP | 3644885 A1 | 5/2020 | |
| EP | 3644886 A1 | 5/2020 | |
| EP | 3749239 A1 | 12/2020 | |
| JP | 2010520770 A | 6/2010 | |
| JP | 2015158461 A * | 9/2015 | ............. G06T 7/004 |
| MX | PA03005028 A | 1/2004 | |
| MX | PA03000137 A | 9/2004 | |
| MX | PA03006874 A | 9/2004 | |
| MX | 225663 B | 1/2005 | |
| MX | 226292 | 2/2005 | |
| MX | PA03010507 A | 7/2005 | |
| MX | PA05011725 A | 5/2006 | |
| MX | 06011286 | 3/2007 | |
| MX | 246862 B | 6/2007 | |
| MX | 2007006441 A | 8/2007 | |
| MX | 265247 | 3/2009 | |
| MX | 284569 B | 3/2011 | |
| WO | 9206636 A1 | 4/1992 | |
| WO | 2017139593 A1 | 8/2017 | |

OTHER PUBLICATIONS

Notice of Reasons for Rejection issued in Japanese Patent Application No. 2020-542153 dated Dec. 21, 2022 with Eng. translation.

* cited by examiner

SYSTEM AND METHOD FOR POSE ESTIMATION OF AN IMAGING DEVICE AND FOR DETERMINING THE LOCATION OF A MEDICAL DEVICE WITH RESPECT TO A TARGET

CROSS-REFERENCE TO RELATED APPLICATIONS

This application is a Continuation of U.S. patent application Ser. No. 16/270,246, filed Feb. 7, 2019, now U.S. Pat. No. 10,893,842, which claims the benefit of the filing date of provisional U.S. Patent Application No. 62/628,017, filed Feb. 8, 2018, provisional U.S. Patent Application No. 62/641,777, filed Mar. 12, 2018, and U.S. patent application Ser. No. 16/022,222, filed Jun. 28, 2018, the entire contents of each of which are incorporated herein by reference.

BACKGROUND

The disclosure relates to the field of imaging, and particularly to the estimation of a pose of an imaging device and to three-dimensional imaging of body organs.

Pose estimation of an imaging device, such as a camera or a fluoroscopic device, may be required or used for variety of applications, including registration between different imaging modalities or the generation of augmented reality. One of the known uses of a pose estimation of an imaging device is the construction of a three-dimensional volume from a set of two-dimensional images captured by the imaging device while in different poses. Such three-dimensional construction is commonly used in the medical field and has a significant impact.

There are several commonly applied medical methods, such as endoscopic procedures or minimally invasive procedures, for treating various maladies affecting organs including the liver, brain, heart, lung, gall bladder, kidney and bones. Often, one or more imaging modalities, such as magnetic resonance imaging, ultrasound imaging, computed tomography (CT), fluoroscopy as well as others are employed by clinicians to identify and navigate to areas of interest within a patient and ultimately targets for treatment. In some procedures, pre-operative scans may be utilized for target identification and intraoperative guidance. However, real-time imaging may be often required in order to obtain a more accurate and current image of the target area. Furthermore, real-time image data displaying the current location of a medical device with respect to the target and its surrounding may be required in order to navigate the medical device to the target in a more safe and accurate manner (e.g., with unnecessary or no damage caused to other tissues and organs).

SUMMARY

According to one aspect of the disclosure, a method for estimating a pose of an imaging device for an image by utilizing a structure of markers is provided. The method includes using at least one hardware processor for generating a probability map for the image indicating a probability of each pixel of the image to belong to a projection of a marker of the structure of markers. The image includes a projection of at least a portion of the structure of markers. The method further includes generating different candidates for the projection of the structure of markers on the image by virtually positioning the imaging device in possible different poses, and identifying the candidate having the highest probability of being the projection of the structure of markers on the image based on the probability map for the image. The pose is estimated based on the virtual pose of the imaging device used to generate the identified candidate.

In an aspect, the method further includes generating a locally deformed version of the candidate to maximize its probability of being the projection of the structure of markers based on the probability map for the image, determining an improved candidate for the projection of the structure of markers on the image based on the locally deformed version of the identified candidate, and determining the virtual pose of the imaging device associated with the improved candidate as the estimated pose of the imaging device for the image.

In an aspect, the generation of a locally deformed version of the candidate and the determination of an improved candidate are iteratively repeated.

In an aspect, each marker of the structure of markers is a sphere. The structure may be a two-dimensional grid, the structure of markers may be of a periodic pattern, and/or a two-dimensional pattern.

In an aspect, the imaging device captures a sequence of images and the method further includes determining a plurality of non-sequential images of the sequence of images, wherein at a first stage, the pose of the imaging device is estimated only for the determined non-sequential images, and at a second stage, reducing the area of possible different poses for virtually positioning the imaging device based on the estimated poses of the imaging device for the determined non-sequential images, wherein the pose of the imaging device for the rest of the images is estimated according to the reduced area.

In yet another aspect, a system for estimating a pose of an imaging device for an image is provided. The system includes a structure of markers, an imaging device, and a computing device. The imaging device acquires an image of at least a portion of the structure of markers. The computing device includes a storage device storing instructions and at least one hardware processor for executing the instructions stored on the storage device. The instructions stored include instructions for generating a probability map for the image indicating a probability of each pixel of the image to belong to a projection of a marker of the structure of markers, generating different candidates for the projection of the structure of markers on the image by virtually positioning the imaging device in possible different poses, and identifying the candidate having the highest probability of being the projection of the structure of markers on the image based on the probability map for the image.

In an aspect, the storage device has further instructions stored thereon for generating a locally deformed version of the candidate to locally maximize its probability of being the projection of the structure of markers based on the probability map for the image, and determining an improved candidate for the projection of the structure of markers on the image based on the locally deformed version.

Each marker of the structure of markers may be a radio-opaque sphere. In an aspect, the structure of markers is grid. The structure of markers may be of a two-dimensional pattern.

In an aspect, the imaging device is a standard fluoroscopic imaging device.

In yet another aspect of the disclosure, a system for estimating a pose of an imaging device for an image is provided. The image includes a structure of markers. The system includes a computing device including a storage device storing instructions and at least one hardware processor for executing the instructions stored on the storage device. The instructions stored include instructions for generating a probability map for the image indicating a probability of each pixel of the image to belong to a projection of a marker of the structure of markers, generating different candidates for the projection of the structure of markers on the image by virtually positioning the imaging device in possible different poses, and identifying the candidate having the highest probability of being the projection of the structure of markers on the image based on the probability map for the image.

In an aspect, the storage device has further instructions stored thereon for generating a locally deformed version of the candidate to locally maximize its probability of being the projection of the structure of markers based on the probability map for the image, and determining an improved candidate for the projection of the structure of markers on the image based on the locally deformed version.

In an aspect, the system includes a structure of markers, where each marker of the structure of markers is a radio-opaque sphere. The structure of markers may be a grid or a two-dimensional pattern.

In an aspect, the storage device has further instructions stored thereon for determining a plurality of non-sequential images of a sequence of images, wherein at a first stage, the pose of the imaging device is estimated only for the determined non-sequential images, and at a second stage, reducing the area of possible different poses for virtually positioning the imaging device based on the estimated poses of the imaging device for the determined non-sequential images, wherein the pose of the imaging device for the rest of the images is estimated according to the reduced area.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

DETAILED DESCRIPTION

Figure 1:
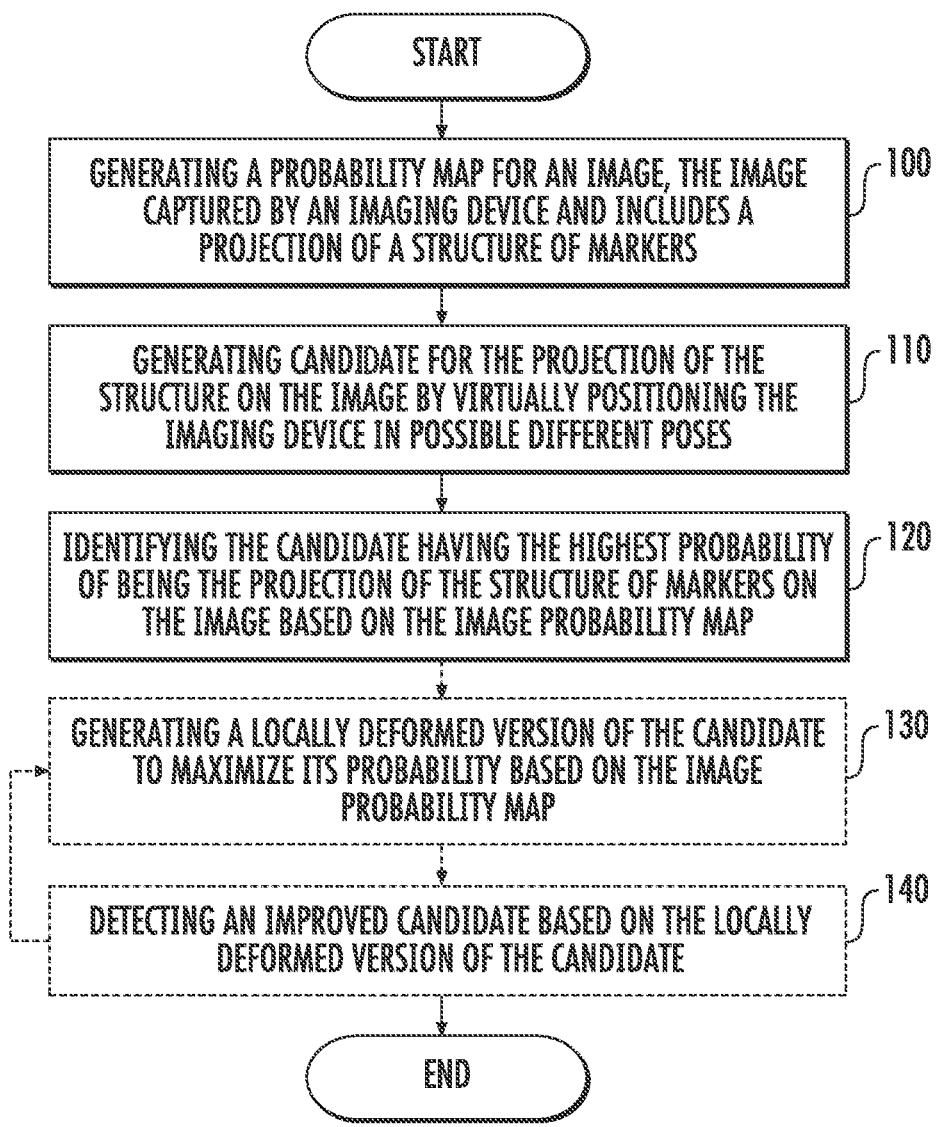
FIG. 1 is a flow chart of a method for estimating the pose of an imaging device by utilizing a structure of markers in accordance with one aspect of the disclosure.

Prior art methods and systems for pose estimation may be inappropriate for real time use, inaccurate or non-robust. Therefore, there is a need for a method and system, which provide a relatively fast, accurate and robust pose estimation, particularly in the field of medical imaging.

In order to navigate medical devices to a remote target for example, for biopsy or treatment, both the medical device and the target should be visible in some sort of a three-dimensional guidance system. When the target is a small soft-tissue object, such as a tumor or a lesion, an X-ray volumetric reconstruction is needed in order to be able to identify it. Several solutions exist that provide three-dimensional volume reconstruction such as CT and Cone-beam CT which are extensively used in the medical world. These machines algorithmically combine multiple X-ray projections from known, calibrated X-ray source positions into three dimensional volume in which, inter alia, soft-tissues are visible. For example, a CT machine can be used with iterative scans during procedure to provide guidance through the body until the tools reach the target. This is a tedious procedure as it requires several full CT scans, a dedicated CT room and blind navigation between scans. In addition, each scan requires the staff to leave the room due to high-levels of ionizing radiation and exposes the patient to such radiation. Another option is a Cone-beam CT machine which is available in some operation rooms and is somewhat easier to operate, but is expensive and like the CT only provides blind navigation between scans, requires multiple iterations for navigation and requires the staff to leave the room. In addition, a CT-based imaging system is extremely costly, and in many cases not available in the same location as the location where a procedure is carried out.

A fluoroscopic imaging device is commonly located in the operating room during navigation procedures. The standard fluoroscopic imaging device may be used by a clinician, for example, to visualize and confirm the placement of a medical device after it has been navigated to a desired location. However, although standard fluoroscopic images display highly dense objects such as metal tools and bones as well as large soft-tissue objects such as the heart, the fluoroscopic images have difficulty resolving small soft-tissue objects of interest such as lesions. Furthermore, the fluoroscope image is only a two-dimensional projection, while in order to accurately and safely navigate within the body, a volumetric or three-dimensional imaging is required.

An endoscopic approach has proven useful in navigating to areas of interest within a patient, and particularly so for areas within luminal networks of the body such as the lungs. To enable the endoscopic, and more particularly the bronchoscopic, approach in the lungs, endobronchial navigation systems have been developed that use previously acquired MRI data or CT image data to generate a three dimensional rendering or volume of the particular body part such as the lungs.

The resulting volume generated from the MRI scan or CT scan is then utilized to create a navigation plan to facilitate the advancement of a navigation catheter (or other suitable medical device) through a bronchoscope and a branch of the bronchus of a patient to an area of interest. A locating system, such as an electromagnetic tracking system, may be utilized in conjunction with the CT data to facilitate guidance of the navigation catheter through the branch of the bronchus to the area of interest. In certain instances, the navigation catheter may be positioned within one of the airways of the branched luminal networks adjacent to, or within, the area of interest to provide access for one or more medical instruments.

As another example, minimally invasive procedures, such as laparoscopy procedures, including robotic-assisted surgery, may employ intraoperative fluoroscopy in order to increase visualization, e.g., for guidance and lesion locating, or in order to prevents injury and complications.

Therefore, a fast, accurate and robust three-dimensional reconstruction of images is required, which is generated based on a standard fluoroscopic imaging performed during medical procedures.

FIG. 1 illustrates a flow chart of a method for estimating the pose of an imaging device by utilizing a structure of markers in accordance with one aspect of the disclosure. In a step 100, a probability map may be generated for an image captured by an imaging device. The image includes a projection of a structure of markers. The probability map may indicate the probability of each pixel of the image to belong to the projection of a marker of the structure of markers. In some embodiments, the structure of markers may be of a two-dimensional pattern. In some embodiments, the structure of markers may be of a periodic pattern, such as a grid. The image may include a projection of at least a portion of the structure of markers.

Figure 2A:
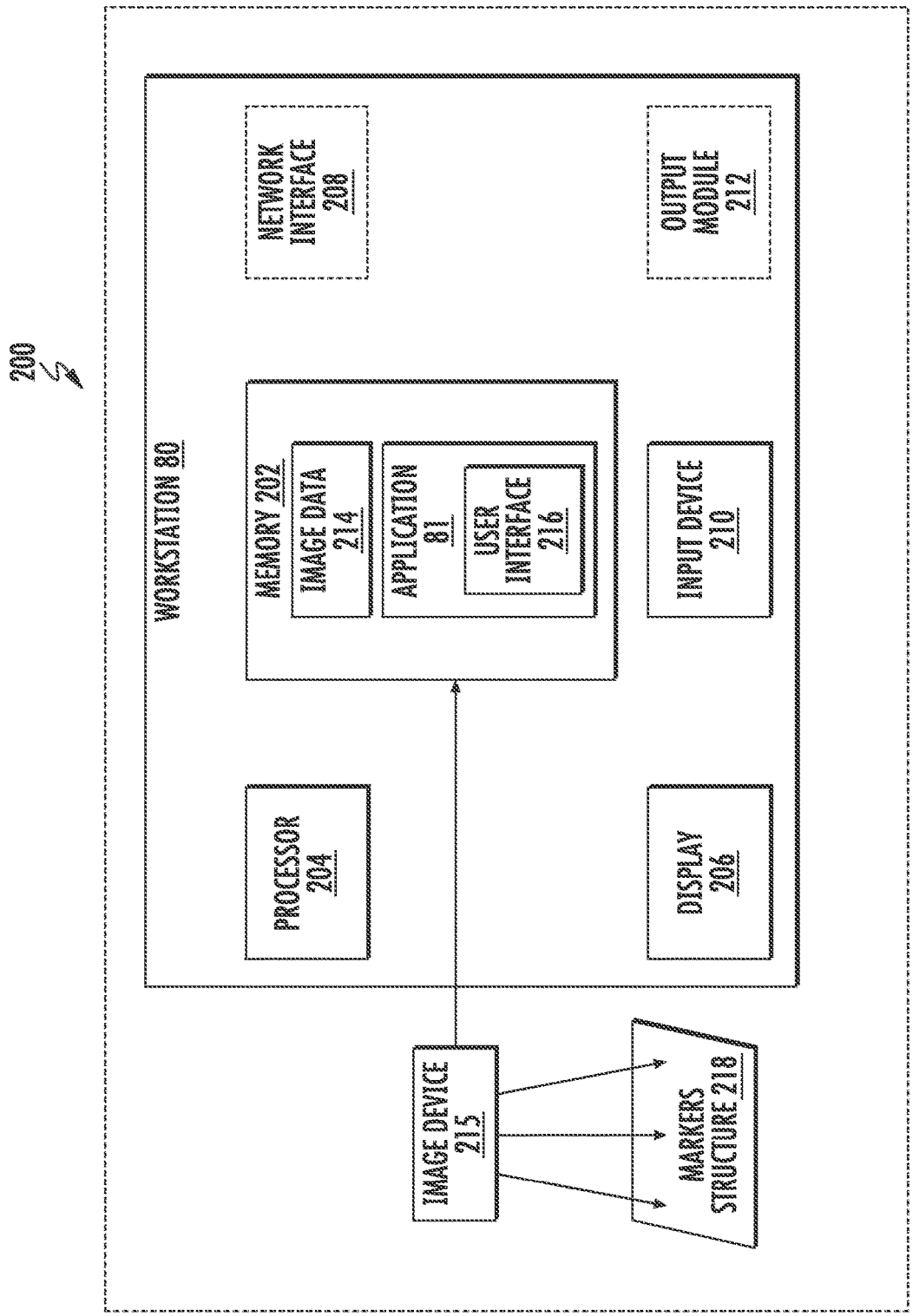
FIG. 2A is a schematic diagram of a system configured for use with the method of FIG. 1 in accordance with one aspect of the disclosure.
Figure 2B:
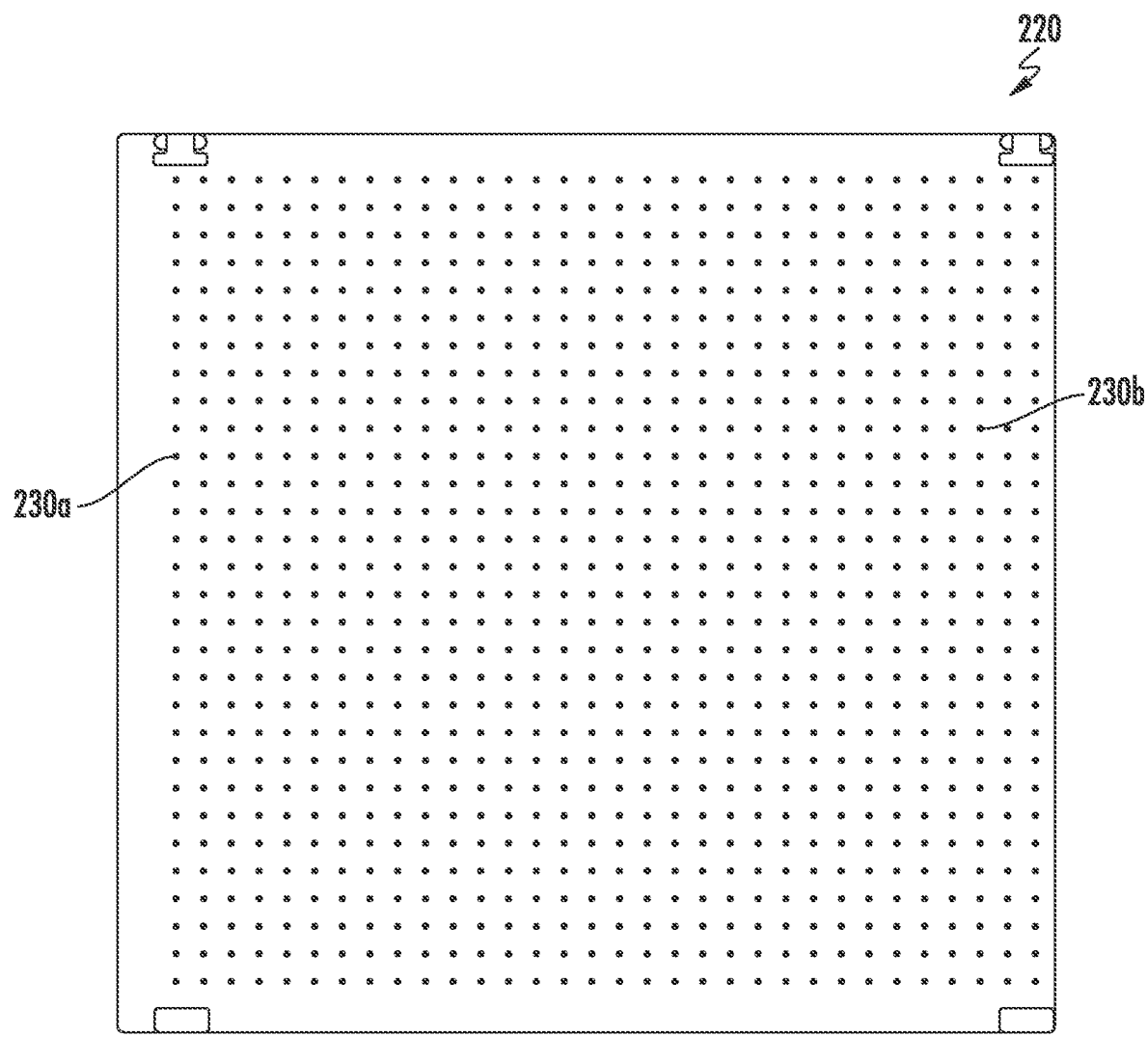
FIG. 2B is a schematic illustration of a two-dimensional grid structure of sphere markers in accordance with one aspect of the disclosure.
Figure 3:
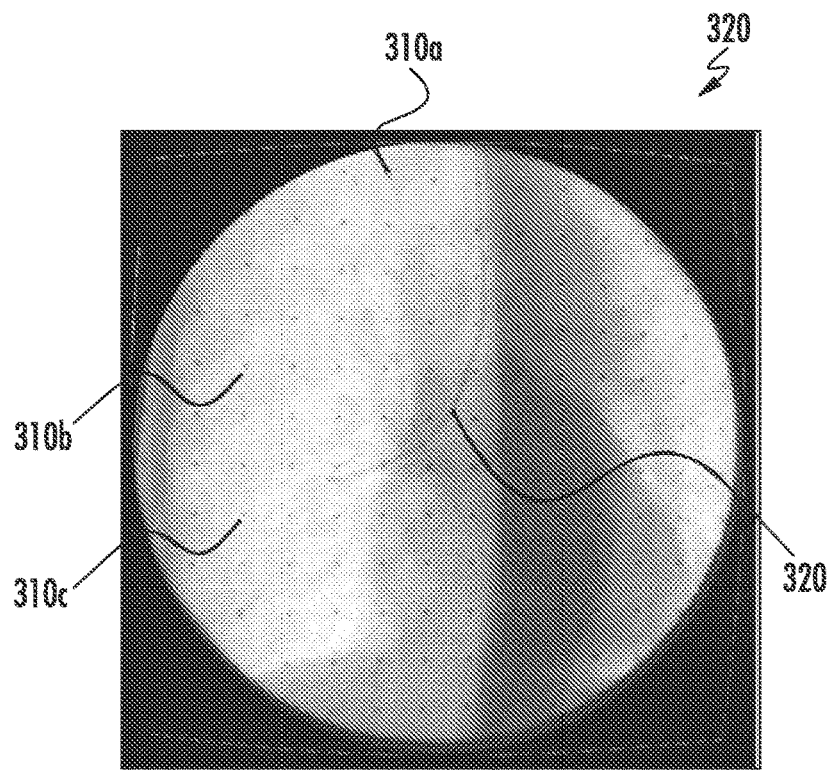
FIG. 3 shows an exemplary image captured by a fluoroscopic device of an artificial chest volume of a Multipurpose Chest Phantom N1 "LUNGMAN", by Kyoto Kagaku, placed over the grid structure of radio-opaque markers of FIG. 2B.

Reference is now made to FIGS. 2B and 3. FIG. 2B is a schematic illustration of a two-dimensional (2D) grid structure of sphere markers 220 in accordance with the disclosure. FIG. 3 is an exemplary image 300 captured by a fluoroscopic device of an artificial chest volume of a Multipurpose Chest Phantom N1 "LUNGMAN", by Kyoto Kagaku, placed over the 2D grid structure of sphere markers 220 of FIG. 2B. 2D grid structure of sphere markers 220 includes a plurality of sphere shaped markers, such as sphere markers 230a and 230b, arranged in a two-dimensional grid pattern. Image 300 includes a projection of a portion of 2D grid structure of sphere markers 220 and a projection of a catheter 320. The projection of 2D grid structure of sphere markers 220 on image 300 includes projections of the sphere markers, such as sphere marker projections 310a, 310b and 310c.

Figure 4:
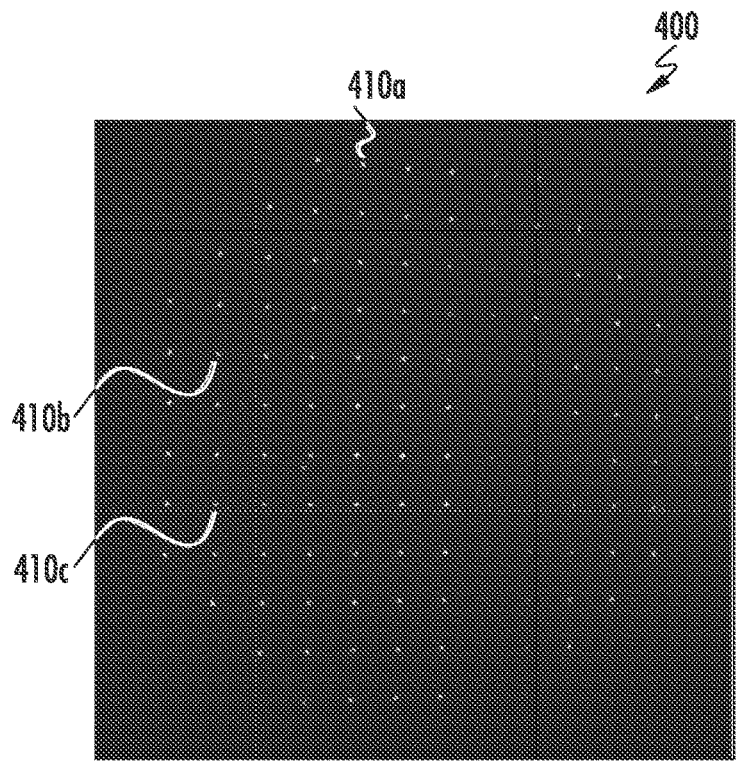
FIG. 4 is a probability map generated for the image of FIG. 3 in accordance with one aspect of the disclosure.

The probability map may be generated, for example, by feeding the image into a simple marker (blob) detector, such as a Harris corner detector, which outputs a new image of smooth densities, corresponding to the probability of each pixel to belong to a marker. FIG. 4 illustrates a probability map 400 generated for image 300 of FIG. 3. Probability map 400 includes pixels or densities, such as densities 410a, 410b and 410c, which correspond accordingly to markers 310a, 310b and 310c. In some embodiments, the probability map may be downscaled (e.g., reduced in size) in order to make the required computations more simple and efficient.

Figure 5A:
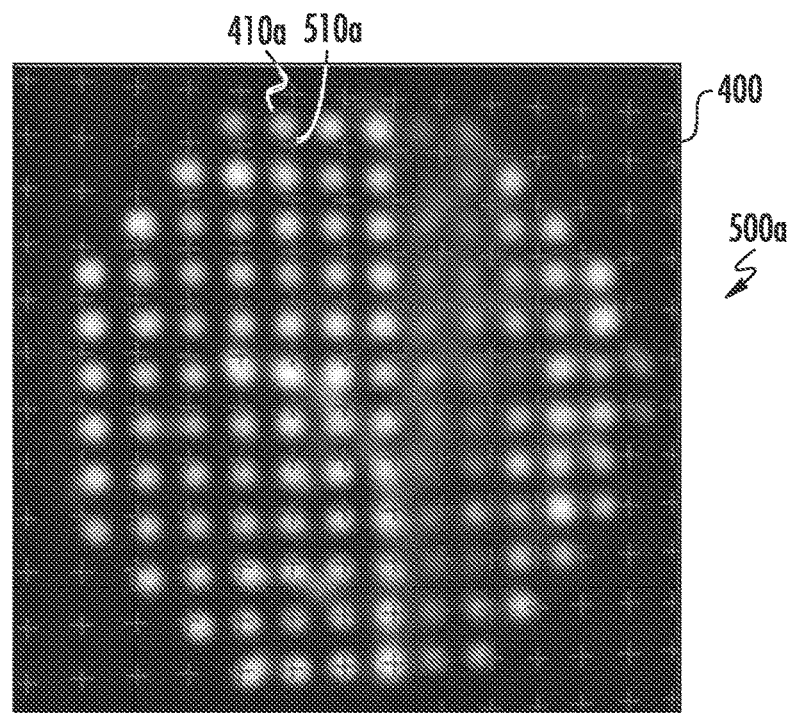
FIGS. 5A-5C show different exemplary candidates for the projection of the 2D grid structure of sphere markers of FIG. 2B on the image of FIG. 3 overlaid on the probability map of FIG. 4.
Figure 5B:
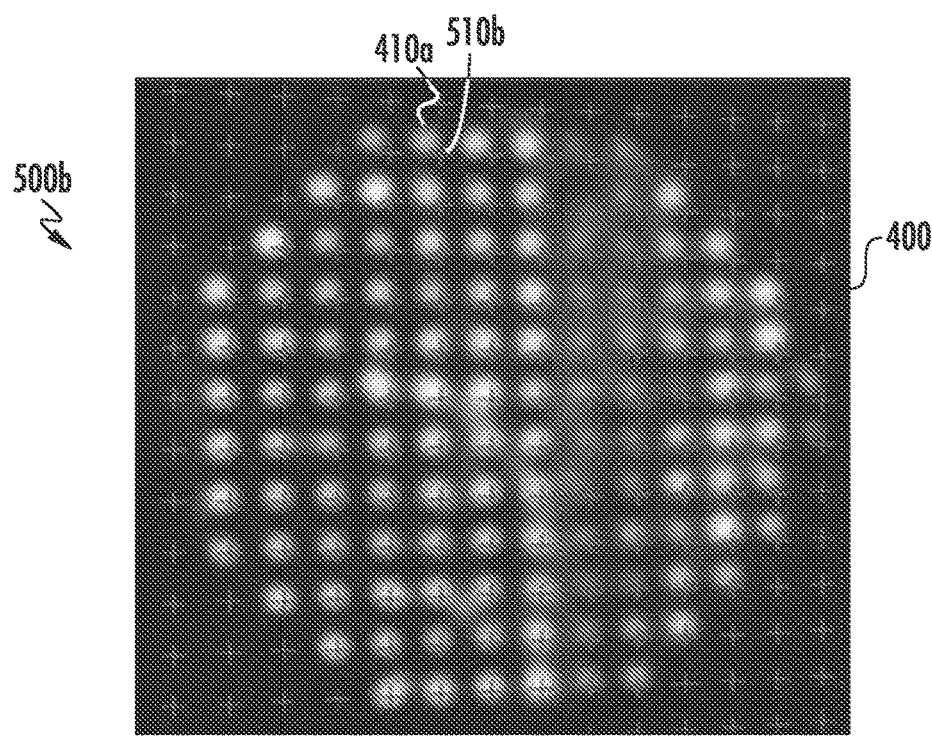
Figure 5C:
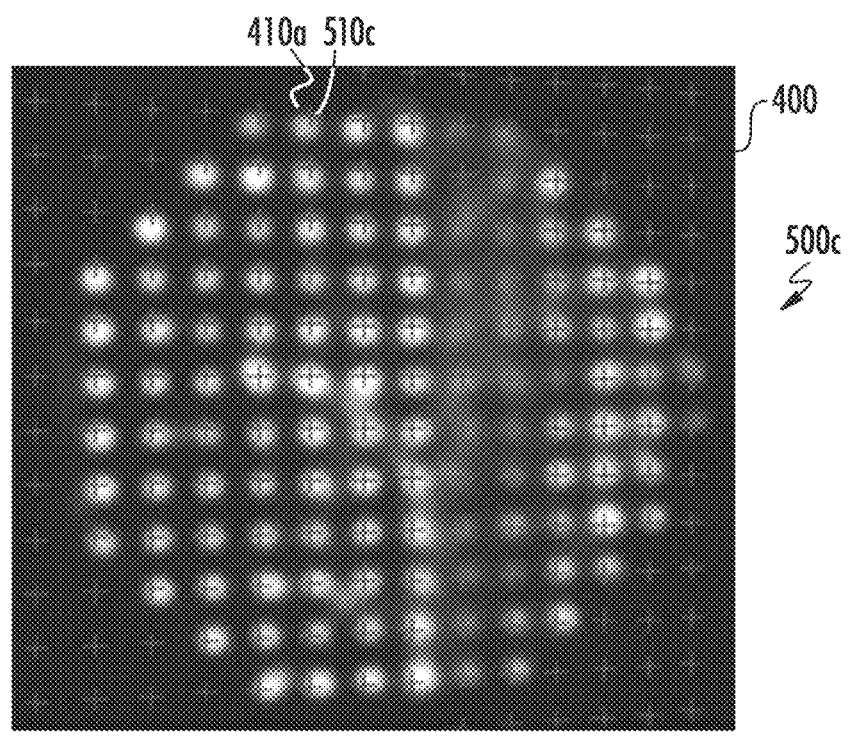
Figure 6A:
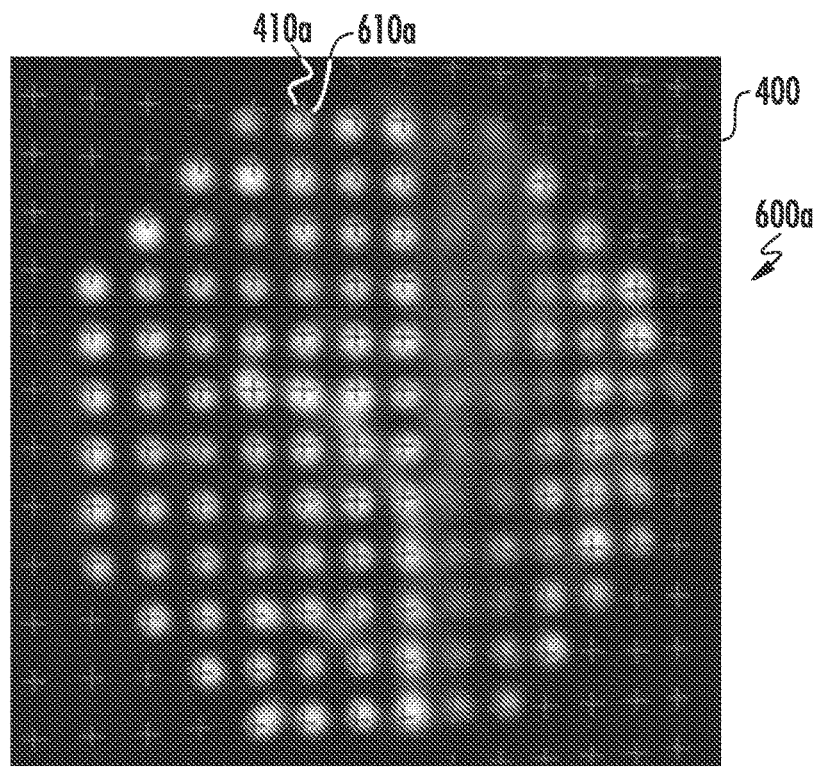
FIG. 6A shows a selected candidate for the projection of the 2D grid structure of sphere markers of FIG. 2B on the image of FIG. 3, overlaid on the probability map of FIG. 4 in accordance with one aspect of the disclosure.
Figure 6B:
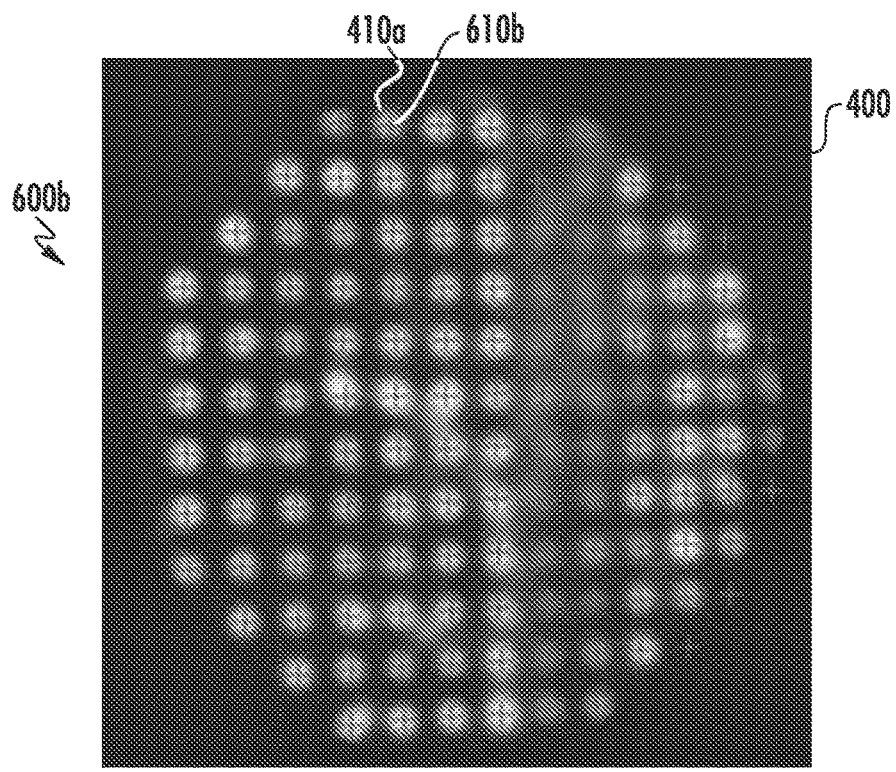
FIG. 6B shows an improved candidate for the projection of the 2D grid structure of sphere markers of FIG. 2B on the image of FIG. 3, overlaid on the probability map of FIG. 4 in accordance with one aspect of the disclosure.
Figure 6C:
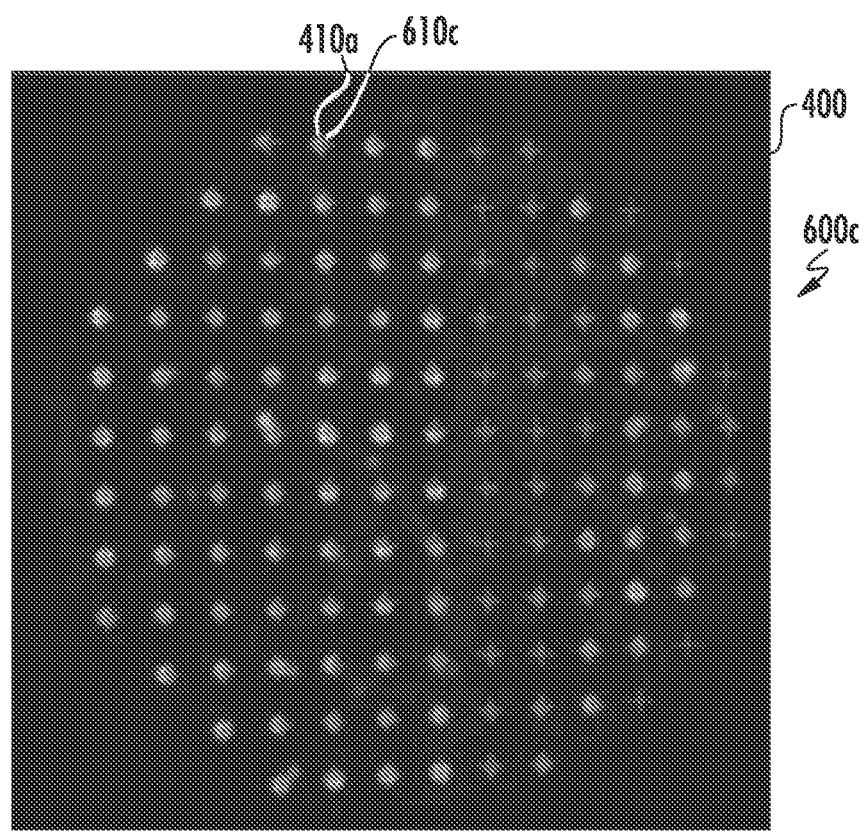
FIG. 6C shows a further improved candidate for the projection of the 2D grid structure of sphere markers of FIG. 2B on image 300 of FIG. 3, overlaid on the probability map of FIG. 4 in accordance with one aspect of the disclosure.

It should be noted that probability map 400, as shown in FIGS. 5A-6B is downscaled by four and probability map 400 as shown in FIG. 6C is downscaled by two.

In a step 110, different candidates may be generated for the projection of the structure of markers on the image. The different candidates may be generated by virtually positioning the imaging device in a range of different possible poses. By "possible poses" of the imaging device, it is meant three-dimensional positions and orientations of the imaging device. In some embodiments, such a range may be limited according to the geometrical structure and/or degrees of freedom of the imaging device. For each such possible pose, a virtual projection of at least a portion of the structure of markers is generated, as if the imaging device actually captured an image of the structure of markers while positioned at that pose.

In a step 120, the candidate having the highest probability of being the projection of the structure of markers on the image may be identified based on the image probability map. Each candidate, e.g., a virtual projection of the structure of markers, may be overlaid or associated to the probability map. A probability score may be then determined or associated with each marker projection of the candidate. In some embodiments, the probability score may be positive or negative, e.g., there may be a cost in case virtual markers projections falls within pixels of low probability. The probability scores of all of the markers projections of a candidate may be then summed and a total probability score may be determined for each candidate. For example, if the structure of markers is a two-dimensional grid, then the projection will have a grid form. Each point of the projection grid would lie on at least one pixel of the probability map. A 2D grid candidate will receive the highest probability score if its points lie on the highest density pixels, that is, if its points lie on projections of the centeres of the markers on the image. The candidate having the highest probability score may be determined as the candidate which has the highest probability of being the projection of the structure of markers on the image. The pose of the imaging device for the image may be then estimated based on the virtual pose of the imaging device used to generate the identified candidate.

FIGS. 5A-5C illustrate different exemplary candidates 500a-c for the projection of 2D grid structure of sphere markers 220 of FIG. 2B on image 300 of FIG. 3 overlaid on probability map 400 of FIG. 4. Candidates 500a, 500b and 500c are indicated as a grid of plus signs ("+"), while each such sign indicates the center of a projection of a marker. Candidates 500a, 500b and 500c are virtual projections of 2D grid structure of sphere markers 220, as if the fluoroscope used to capture image 300 is located at three different poses associated correspondingly with these projections. In this example, candidate 500a was generated as if the fluoroscope is located at: position [0, −50, 0], angle: −20 degrees. Candidate 500b was generated as if the fluoroscope is located at: position [0, −10, 0], angle: −20 degrees. Candidate 500c was generated as if the fluoroscope is located at: position [7.5, −40, 11.25], angle: −25 degrees. The above-mentioned coordinates are with respect to 2D grid structure of sphere markers 220. Densities 410a of probability map 400 are indicated in FIGS. 5A-5C. Plus signs 510a, 510b and 510c are the centers of the markers projections of candidates 500a, 500b and 500c correspondingly, which are the ones closest to densities 410a. One can see that plus sign 510c is the sign which best fits densities 410a and therefore would receive the highest probability score among signs 510a, 510b and 510c of candidates 500a, 500b and 500c correspondingly. One can further see that accordingly, candidate 500*c* would receive the highest probability score since its markers projections best fit probability map 400. Thus, among these three exemplary candidates, 500*a*, 500*b* and 500*c*, candidate 500*c* would be identified as the candidate with the highest probability of being the projection of 2D grid structure of sphere markers 220 on image 300.

Further steps may be performed in order to refine the above described pose estimation. In an optional step 130, a locally deformed version of the candidate may be generated in order to maximize its probability of being the projection of the structure of markers on the image. The locally deformed version may be generated based on the image probability map. A local search algorithm may be utilized to deform the candidate so that it would maximize its score. For example, in case the structure of markers is a 2D grid, each 2D grid point may be treated individually. Each point may be moved towards the neighbouring local maxima on the probability map using gradient ascent method.

In an optional step 140, an improved candidate for the projection of the structure of markers on the image may be detected based on the locally deformed version of the candidate. The improved candidate is determined such that it fits (exactly or approximately) the locally deformed version of the candidate. Such improved candidate may be determined by identifying a transformation that will fit a new candidate to the local deformed version, e.g., by using homography estimation methods. The virtual pose of the imaging device associated with the improved candidate may be then determined as the estimated pose of the imaging device for the image.

In some embodiments, the generation of a locally deformed version of the candidate and the determination of an improved candidate may be iteratively repeated. These steps may be iteratively repeated until the process converges to a specific virtual projection of the structure of markers on the image, which may be determined as the improved candidate. Thus, since the structure of markers converges as a whole, false local maxima is avoided. In an aspect, as an alternative to using a list of candidates and finding an optimal candidate for estimating the camera pose, the camera pose may be estimated by solving a homography that transforms a 2D fiducial structure in 3D space into image coordinates that matches the fiducial probability map generated from the imaging device output.

FIG. 6A shows a selected candidate 600*a*, for projection of 2D grid structure of sphere markers 220 of FIG. 2B on image 300 of FIG. 3, overlaid on probability map 400 of FIG. 4. FIG. 6B shows an improved candidate 600B, for the projection of 2D grid structure of sphere markers 220 of FIG. 2B on image 300 of FIG. 3, overlaid on probability map 400 of FIG. 4. FIG. 6C shows a further improved candidate 600*c*, for the projection of 2D grid structure of sphere markers 220 of FIG. 2B on image 300 of FIG. 3, overlaid on probability map 400 of FIG. 4. As described above, the identified or selected candidate is candidate 500*c*, which is now indicated 600*a*. Candidate 600*b* is the improved candidate which was generated based on a locally deformed version of candidate 600*a* according to the method disclosed above. Candidate 600*c* is a further improved candidate with respect to candidate 600*b*, generated by iteratively repeating the process of locally deforming the resulting candidate and determining an approximation to maximize the candidate probability. FIG. 6C illustrates the results of refined candidates based on a higher resolution probability map. In an aspect, this is done after completing a refinement step using the down-sampled version of the probability map. Plus signs 610*a*, 610*b* and 610*c* are the centers of the markers projections of candidates 600*a*, 600*b* and 600*c* correspondingly, which are the ones closest to densities 410*a* of probability map 400. One can see how the candidates for the projection of 2D grid structure of sphere markers 220 on image 300 converge to the candidate of the highest probability according to probability map 400.

In some embodiments, the imaging device may be configured to capture a sequence of images. A sequence of images may be captured, automatically or manually, by continuously sweeping the imaging device at a certain angle. When pose estimation of a sequence of images is required, the estimation process may become more efficient by reducing the range or area of possible virtual poses for the imaging device. A plurality of non-sequential images of the sequence of images may be then determined. For example, the first image in the sequence, the last image, and one or more images in-between. The one or more images in-between may be determined such that the sequence is divided into equal image portions. At a first stage, the pose of the imaging device may be estimated only for the determined non-sequential images. At a second stage, the area or range of possible different poses for virtually positioning the imaging device may be reduced. The reduction may be performed based on the estimated poses of the imaging device for the determined non-sequential images. The pose of the imaging device for the rest of the images may be then estimated according to the reduced area or range. For example, the pose of the imaging device for the first and tenth images of the sequence are determined at the first stage. The pose of the imaging device for the second to ninth images must be along a feasible and continuous path between its pose for the first image and its pose for the tenth image, and so on.

In some embodiments, geometrical parameters of the imaging device may be pre-known, or pre-determined, such as the field of view of the source, height range, rotation angle range and the like, including the device degrees of freedom (e.g., independent motions allowed). In some embodiments, such geometrical parameters of the imaging device may be determined in real-time while estimating the pose of the imaging device for the captured images. Such information may be also used to reduce the area or range of possible poses. In some embodiments, a user practicing the disclosed disclosure may be instructed to limit the motion of the imaging device to certain degrees of freedom or to certain ranges of motion for the sequence of images. Such limitations may be also considered when determining the imaging device possible poses and thus may be used to make the imaging device pose estimation faster.

In some embodiments, an image pre-processing methods may be first applied to the one or more images in order to correct distortions and/or enhance the visualization of the projection of the structure of markers on the image. For example, in case the imaging device is a fluoroscope, correction of "pincushion" distortion, which slightly warps the image, may be performed. This distortion may be automatically addressed by modelling the warp with a polynomial surface and applying compatible warp which will cancel out the pincushion effect. In case a grid of metal spheres is used, the image may be inversed in order to enhance the projections of the markers. In addition, the image may be blurred using Gaussian filter with sigma value equal, for example, to one half of the spheres diameter, in order to facilitate the search and evaluation of candidates as disclosed above.

In some embodiments, one or more models of the imaging device may be calibrated to generate calibration data, such as a data file, which may be used to automatically calibrate the specific imaging device. The calibration data may include data referring to the geometric calibration and/or distortion calibration, as disclosed above. In some embodiments, the geometric calibration may be based on data provided by the imaging device manufacturer. In some embodiments, a manual distortion calibration may be performed once for a specific imaging device. In an aspect, the imaging device distortion correction can be calibrated as a preprocessing step during every procedure as the pincushion distortion may change as a result of imaging device maintenance or even as a result of a change in time.

FIG. 2A illustrates a schematic diagram of a system 200 configured for use with the method of FIG. 1 in accordance with one aspect of the disclosure. System 200 may include a workstation 80, an imaging device 215 and a structure of markers structure 218. In some embodiments, workstation 80 may be coupled with imaging device 215, directly or indirectly, e.g., by wireless communication. Workstation 80 may include a memory 202, a processor 204, a display 206 and an input device 210. Processor or hardware processor 204 may include one or more hardware processors. Workstation 80 may optionally include an output module 212 and a network interface 208. Memory 202 may store an application 81 and image data 214. Application 81 may include instructions executable by processor 204, inter alia, for executing the method of FIG. 1 and a user interface 216. Workstation 80 may be a stationary computing device, such as a personal computer, or a portable computing device such as a tablet computer. Workstation 80 may embed a plurality of computer devices.

Memory 202 may include any non-transitory computer-readable storage media for storing data and/or software including instructions that are executable by processor 204 and which control the operation of workstation 80 and in some embodiments, may also control the operation of imaging device 215. In an embodiment, memory 202 may include one or more solid-state storage devices such as flash memory chips. Alternatively, or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information and which may be accessed by workstation 80.

Application 81 may, when executed by processor 204, cause display 206 to present user interface 216. Network interface 208 may be configured to connect to a network such as a local area network (LAN) consisting of a wired network and/or a wireless network, a wide area network (WAN), a wireless mobile network, a Bluetooth network, and/or the Internet. Network interface 208 may be used to connect between workstation 80 and imaging device 215. Network interface 208 may be also used to receive image data 214. Input device 210 may be any device by means of which a user may interact with workstation 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Imaging device 215 may be any imaging device, which captures 2D images, such as a standard fluoroscopic imaging device or a camera. In some embodiments, markers structure 218, may be a structure of markers having a two-dimensional pattern, such as a grid having two dimensions of width and length (e.g., 2D grid), as shown in FIG. 2B. Using a 2D pattern, as opposed to a 3D pattern, may facilitate the pose estimation process. Furthermore, when for example, a patient is required to lie on markers structure 218 in order to estimate the pose of a medical imaging device while scanning the patient, a 2D pattern would be more convenient for the patient. The markers should be formed such that they will be visible in the imaging modality used. For example, if the imaging device is a fluoroscopic device, then the markers should be made of a material which is at least partially radio-opaque. In some embodiments, the shape of the markers may be symmetric and such that the projection of the markers on the image would be the same at any pose the imaging device may be placed. Such configuration may simplify and enhance the pose estimation process and/or make it more efficient. For example, when the imaging device is rotated around the markers structure, markers having a rotation symmetry may be preferred, such as spheres. The size of the markers structure and/or the number of markers in the structure may be determined according to the specific use of the disclosed systems and methods. For example, if the pose estimation is used to construct a 3D volume of an area of interest within a patient, then the markers structure may be of a size similar or larger than the size of the area of interest. In some embodiments, the pattern of markers structure 218 may be two-dimensional and/or periodic, such as a 2D grid. Using a periodic and/or of a two-dimensional pattern structure of markers may further enhance and facilitate the pose estimation process and make it more efficient.

Referring now to FIG. 2B, 2D grid structure of sphere markers 220 has a 2D periodic pattern of a grid and includes symmetric markers in the shape of a sphere. Such a configuration simplifies and enhances the pose estimation process, as described in FIG. 1, specifically when generating the virtual candidates for the markers structure projection and when determining the optimal one. The structure of markers, as a fiducial, should be positioned in a stationary manner during the capturing of the one or more images. In an exemplary 2D grid structure of sphere markers such as described above, used in medical imaging of the lungs area, the sphere markers diameter may be 2±0.2 mm and the distance between the spheres may be about 15±0.15 mm isotropic.

Referring now back to FIG. 2A, imaging device 215 may capture one or more images (i.e., a sequence of images) such that at least a projection of a portion of markers structure 218 is shown in each image. The image or sequence of images captured by imaging device 215 may be then stored in memory 202 as image data 214. The image data may be then processed by processor 204 and according to the method of FIG. 1, to determine the pose of imaging device 215. The pose estimation data may be then output via output module 212, display 206 and/or network interface 208. Markers structure 218 may be positioned with respect to an area of interest, such as under an area of interest within the body of a patient going through a fluoroscopic scan. Markers structure 218 and the patient will then be positioned such that the one or more images captured by imaging device 215 would capture the area of interest and a portion of markers structure 218. If required, once the pose estimation process is complete, the projection of markers structure 218 on the images may be removed by using well known methods. One such method is described in commonly-owned U.S. patent application Ser. No. 16/259,612, entitled: "IMAGE RECONSTRUCTION SYSTEM AND METHOD", filed on Jan. 28, 2019, by Alexandroni et al., the entire content of which is hereby incorporated by reference.

Figure 7:
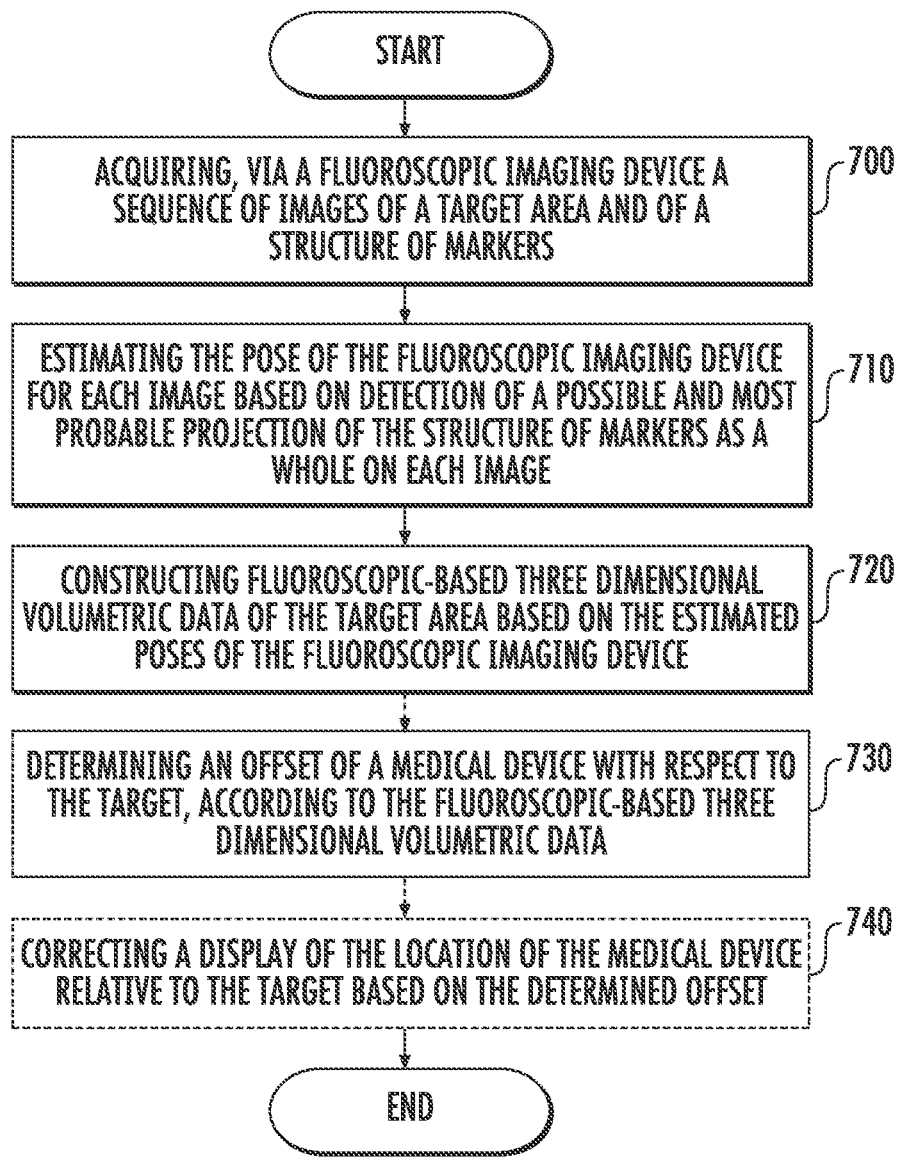
FIG. 7 is a flow chart of an exemplary method for constructing fluoroscopic three-dimensional volumetric data in accordance with one aspect of the disclosure.

FIG. 7 is a flow chart of an exemplary method for constructing fluoroscopic three-dimensional volumetric data in accordance with the disclosure. A method for constructing fluoroscopic-based three-dimensional volumetric data of a target area within a patient from two dimensional fluoroscopic images, is hereby disclosed. In step 700, a sequence of images of the target area and of a structure of markers is acquired via a fluoroscopic imaging device. The structure of markers may be the two-dimensional structure of markers described with respect to FIGS. 1, 2A and 2B. The structure of markers may be positioned between the patient and the fluoroscopic imaging device. In some embodiments, the target area may include, for example, at least a portion of the lungs, and as exemplified with respect to the system of FIG. 8. In some embodiments, the target is a soft-tissue target, such as within a lung, kidney, liver and the like.

In a step 710, a pose of the fluoroscopic imaging device for at least a plurality of images of the sequence of images may be estimated. The pose estimation may be performed based on detection of a possible and most probable projection of the structure of markers as a whole on each image of the plurality of images, and as described with respect to FIG. 1.

In some embodiments, other methods for estimating the pose of the fluoroscopic device may be used. There are various known methods for determining the poses of imaging devices, such as an external angle measuring device or based on image analysis. Some of such devices and methods are particularly described in commonly-owned U.S. Patent Publication No. 2017/0035379, filed on Aug. 1, 2016, by Weingarten et al, the entire content of which is hereby incorporated by reference.

In a step 720, a fluoroscopic-based three-dimensional volumetric data of the target area may be constructed based on the estimated poses of the fluoroscopic imaging device. Exemplary systems and methods for constructing such fluoroscopic-based three-dimensional volumetric data are disclosed in the above commonly-owned U.S. Patent Publication No. 2017/0035379, which is incorporated by reference.

In an optional step 730, a medical device may be positioned in the target area prior to the acquiring of the sequence of images. Thus, the sequence of images and consequently the fluoroscopic-based three-dimensional volumetric data may also include a projection of the medical device in addition to the target. The offset (i.e., $\Delta x$, $\Delta y$ and $\Delta z$) between the medical device and the target may be then determined based on the fluoroscopic-based three-dimensional volumetric data. The target may be visible or better exhibited in the generated three-dimensional volumetric data. Therefore, the target may be detected, automatically, or manually by the user, in the three-dimensional volumetric data. The medical device may be detected, automatically or manually by a user, in the sequence of images, as captured, or in the generated three-dimensional volumetric data. The automatic detection of the target and/or the medical device may be performed based on systems and methods as known in the art and such as described, for example, in commonly-owned U.S. Patent Application No. 62/627,911, titled: "SYSTEM AND METHOD FOR CATHETER DETECTION IN FLUOROSCOPIC IMAGES AND UPDATING DISPLAYED POSITION OF CATHETER", filed on Feb. 8, 2018, by Birenbaum et al. The manual detection may be performed by displaying to the user the three-dimensional volumetric data and/or captured images and requesting his input. Once the target and the medical device are detected in the three-dimensional volumetric data and/or the captures images, their location in the fluoroscopic coordinate system of reference may be obtained and the offset between them may be determined.

The offset between the target and the medical device may be utilized for various medical purposes, including facilitating approach of the medical device to the target area and treatment. The navigation of a medical device to the target area may be facilitated via a locating system and a display. The locating system locates or tracks the motion of the medical device through the patient's body. The display may display the medical device location to the user with respect to the surroundings of the medical device within the patient's body and the target. The locating system may be, for example, an electromagnetic or optic locating system, or any other such system as known in the art. When, for example, the target area includes a portion of the lungs, the medical device may be navigated to the target area through the airways luminal network and as described with respect to FIG. 8.

Figure 8:
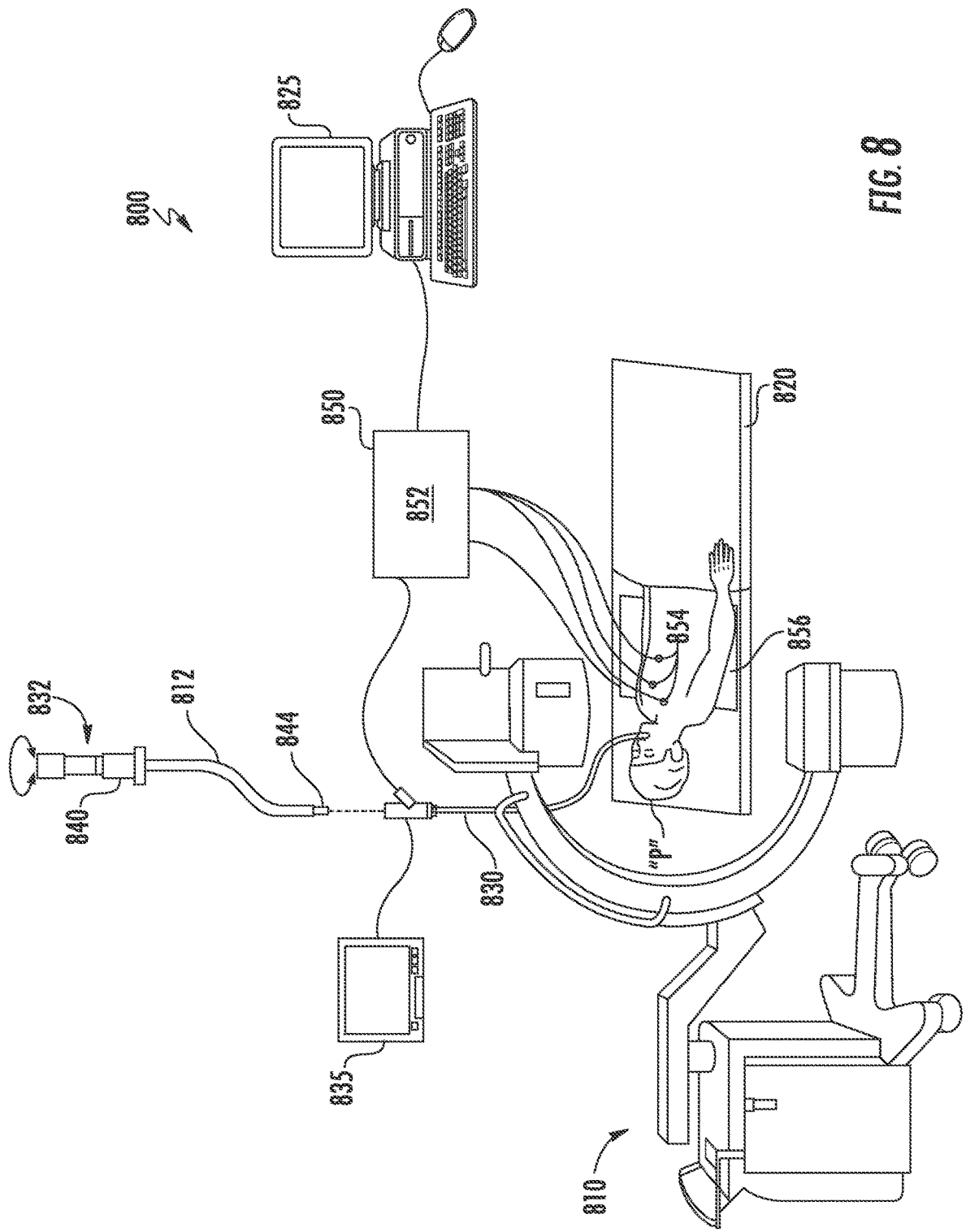
FIG. 8 is a view of one illustrative embodiment of an exemplary system for constructing fluoroscopic-based three-dimensional volumetric data in accordance with the disclosure.

In an optional step 740, a display of the location of the medical device with respect to the target may be corrected based on the determined offset between the medical device and the target. In some embodiments, a 3D rendering of the target area may be displayed on the display. The 3D rendering of the target area may be generated based on CT volumetric data of the target area which was acquired previously, e.g., prior to the current procedure or operation (e.g., preoperative CT). In some embodiments, the locating system may be registered to the 3D rendering of the target, such as described, for example, with respect to FIG. 8 below. The correction of the offset between the medical device and the target may be then performed by updating the registration of the locating system to the 3D rendering. Generally, to perform such updating, a transformation between coordinate system of reference of the fluoroscopic images and the coordinate system of reference of the locating system should be known. The geometrical positioning of the structure of markers with respect to the locating system may determine such a transformation. In some embodiments, and as shown in the embodiment of FIG. 8, the structure of markers and the locating system are positioned such that the same coordinate system of reference would apply to both, or such that the one would be only a translated version of the other.

In some embodiments, the updating of the registration of the locating system to the 3D rendering (e.g., CT-base) may be performed in a local manner and/or in a gradual manner. For example, the registration may be updated only in the surroundings of the target, e.g., only within a certain distance from the target. This is since the update may be less accurate when not performed around the target. In some embodiments, the updating may be performed in a gradual manner, e.g., by applying weights according to distance from the target. In addition to accuracy considerations, such gradual updating may be more convenient or easier for the user to look at, process and make the necessary changes during procedure, than abrupt change in the medical device location on the display.

In some embodiments, the patient may be instructed to stop breathing (or caused to stop breathing) during the capture of the images in order to prevent movements of the target area due to breathing. In other embodiments, methods for compensating breathing movements during the capture of the images may be performed. For example, the estimated poses of the fluoroscopic device may be corrected according to the movements of a fiducial marker placed in the target area. Such a fiducial may be a medical device, e.g., a catheter, placed in the target area. The movement of the catheter, for example, may be determined based on the locating system. In some embodiments, a breathing pattern of the patient may be determined according to the movements of a fiducial marker, such as a catheter, located in the target area. The movements may be determined via a locating system. Based on that pattern, only images of inhale or exhale may be considered when determining the pose of the imaging device.

In embodiments, as described above, for each captured frame, the imaging device three-dimensional position and orientation are estimated based on a set of static markers positioned on the patient bed. This process requires knowledge about the markers 3D positions in the volume, as well as the compatible 2D coordinates of the projections in the image plane. Adding one or more markers from different planes in the volume of interest may lead to more robust and accurate pose estimation. One possible marker that can be utilized in such a process is the catheter tip (or other medical device tip positioned through the catheter). The tip is visible throughout the video captured by fluoroscopic imaging and the compatible 3D positions may be provided by a navigation or tracking system (e.g., an electromagnetic navigation tracking system) as the tool is navigated to the target (e.g., through the electromagnetic field). Therefore, the only remaining task is to deduce the exact 2D coordinates from the video frames. As described above, one embodiment of the tip detection step may include fully automated detection and tracking of the tip throughout the video. Another embodiment may implement semi-supervised tracking in which the user manually marks the tip in one or more frames and the detection process computes the tip coordinates for the rest of the frames.

In embodiments, the semi-supervised tracking process may be implemented in accordance with solving each frame at a time by template matching between current frame and previous ones, using optical flow to estimate the tip movement along the video, and/or model-based trackers. Model-based trackers train a detector to estimate the probability of each pixel to belong to the catheter tip, which is followed by a step of combining the detections to a single most probable list of coordinates along the video. One possible embodiment of the model-based trackers involves dynamic programming. Such an optimization approach enables finding a seam (connected list of coordinates along the video frames 3D space—first two dimensions belongs to the image plane and the third axis is time) with maximal probability. Another possible way to achieve a seam of two-dimensional coordinates is training a detector to estimate the tip coordinate in each frame while incorporating a regularization to the loss function of proximity between detections in adjacent frames.

FIG. 8 illustrates an exemplary system 800 for constructing fluoroscopic-based three-dimensional volumetric data in accordance with the disclosure. System 800 may be configured to construct fluoroscopic-based three-dimensional volumetric data of a target area including at least a portion of the lungs of a patient from 2D fluoroscopic images. System 800 may be further configured to facilitate approach of a medical device to the target area by using Electromagnetic Navigation Bronchoscopy (ENB) and for determining the location of a medical device with respect to the target.

System 800 may be configured for reviewing CT image data to identify one or more targets, planning a pathway to an identified target (planning phase), navigating an extended working channel (EWC) 812 of a catheter assembly to a target (navigation phase) via a user interface, and confirming placement of EWC 812 relative to the target. One such EMN system is the ELECTROMAGNETIC NAVIGATION BRONCHOSCOPY® system currently sold by Medtronic PLC. The target may be tissue of interest identified by review of the CT image data during the planning phase. Following navigation, a medical device, such as a biopsy tool or other tool, may be inserted into EWC 812 to obtain a tissue sample from the tissue located at, or proximate to, the target.

FIG. 8 illustrates EWC 812 which is part of a catheter guide assembly 840. In practice, EWC 812 is inserted into a bronchoscope 830 for access to a luminal network of the patient "P." Specifically, EWC 812 of catheter guide assembly 840 may be inserted into a working channel of bronchoscope 830 for navigation through a patient's luminal network. A locatable guide (LG) 832, including a sensor 844 is inserted into EWC 812 and locked into position such that sensor 844 extends a desired distance beyond the distal tip of EWC 812. The position and orientation of sensor 844 relative to the reference coordinate system, and thus the distal portion of EWC 812, within an electromagnetic field can be derived. Catheter guide assemblies 840 are currently marketed and sold by Medtronic PLC under the brand names SUPERDIMENSION® Procedure Kits, or EDGE™ Procedure Kits, and are contemplated as useable with the disclosure. For a more detailed description of catheter guide assemblies 840, reference is made to commonly-owned U.S. Patent Publication No. 2014/0046315, filed on Mar. 15, 2013, by Ladtkow et al, U.S. Pat. Nos. 7,233,820, and 9,044,254, the entire contents of each of which are hereby incorporated by reference.

System 800 generally includes an operating table 820 configured to support a patient "P," a bronchoscope 830 configured for insertion through the patient's "P's" mouth into the patient's "P's" airways; monitoring equipment 835 coupled to bronchoscope 830 (e.g., a video display, for displaying the video images received from the video imaging system of bronchoscope 830); a locating system 850 including a locating module 852, a plurality of reference sensors 854 and a transmitter mat coupled to a structure of markers 856; and a computing device 825 including software and/or hardware used to facilitate identification of a target, pathway planning to the target, navigation of a medical device to the target, and confirmation of placement of EWC 812, or a suitable device therethrough, relative to the target. Computing device 825 may be similar to workstation 80 of FIG. 2A and may be configured, inter alia, to execute the method of FIG. 1.

A fluoroscopic imaging device 810 capable of acquiring fluoroscopic or x-ray images or video of the patient "P" is also included in this particular aspect of system 800. The images, sequence of images, or video captured by fluoroscopic imaging device 810 may be stored within fluoroscopic imaging device 810 or transmitted to computing device 825 for storage, processing, and display, as described with respect to FIG. 2A. Additionally, fluoroscopic imaging device 810 may move relative to the patient "P" so that images may be acquired from different angles or perspectives relative to patient "P" to create a sequence of fluoroscopic images, such as a fluoroscopic video. The pose of fluoroscopic imaging device 810 relative to patient "P" and for the images may be estimated via the structure of markers and according to the method of FIG. 1. The structure of markers is positioned under patient "P," between patient "P" and operating table 820 and between patient "P" and a radiation source of fluoroscopic imaging device 810. Structure of markers is coupled to the transmitter mat (both indicated 856) and positioned under patient "P" on operating table 820. Structure of markers and transmitter mat 856 are positioned under the target area within the patient in a stationary manner. Structure of markers and transmitter mat 856 may be two separate elements which may be coupled in a fixed manner or alternatively may be manufactured as one unit. Fluoroscopic imaging device 810 may include a single imaging device or more than one imaging device. In embodiments including multiple imaging devices, each imaging device may be a different type of imaging device or the same type. Further details regarding the imaging device 810 are described in U.S. Pat. No. 8,565,858, which is incorporated by reference in its entirety herein.

Computing device 825 may be any suitable computing device including a processor and storage medium, wherein the processor is capable of executing instructions stored on the storage medium. Computing device 825 may further include a database configured to store patient data, CT data sets including CT images, fluoroscopic data sets including fluoroscopic images and video, navigation plans, and any other such data. Although not explicitly illustrated, computing device 825 may include inputs, or may otherwise be configured to receive, CT data sets, fluoroscopic images/video and other data described herein. Additionally, computing device 825 includes a display configured to display graphical user interfaces. Computing device 825 may be connected to one or more networks through which one or more databases may be accessed.

With respect to the planning phase, computing device 825 utilizes previously acquired CT image data for generating and viewing a three dimensional model of the patient's "P's" airways, enables the identification of a target on the three dimensional model (automatically, semi-automatically, or manually), and allows for determining a pathway through the patient's "P's" airways to tissue located at and around the target. More specifically, CT images acquired from previous CT scans are processed and assembled into a three dimensional CT volume, which is then utilized to generate a three dimensional model of the patient's "P's" airways. The three dimensional model may be displayed on a display associated with computing device 825, or in any other suitable fashion. Using computing device 825, various views of the three dimensional model or enhanced two dimensional images generated from the three dimensional model are presented. The enhanced two dimensional images may possess some three dimensional capabilities because they are generated from three dimensional data. The three dimensional model may be manipulated to facilitate identification of target on the three dimensional model or two dimensional images, and selection of a suitable pathway through the patient's "P's" airways to access tissue located at the target can be made. Once selected, the pathway plan, three dimensional model, and images derived therefrom, can be saved and exported to a navigation system for use during the navigation phase(s). One such planning software is the ILOGIC® planning suite currently sold by Medtronic PLC.

With respect to the navigation phase, a six degrees-of-freedom electromagnetic locating or tracking system 850, e.g., similar to those disclosed in U.S. Pat. Nos. 8,467,589, 6,188,355, and published PCT Application Nos. WO 00/10456 and WO 01/67035, the entire contents of each of which are incorporated herein by reference, or other suitable positioning measuring system, is utilized for performing registration of the images and the pathway for navigation, although other configurations are also contemplated. Tracking system 850 includes a locating or tracking module 852, a plurality of reference sensors 854, and a transmitter mat 856. Tracking system 850 is configured for use with a locatable guide 832 and particularly sensor 844. As described above, locatable guide 832 and sensor 844 are configured for insertion through an EWC 182 into a patient's "P's" airways (either with or without bronchoscope 830) and are selectively lockable relative to one another via a locking mechanism.

Transmitter mat 856 is positioned beneath patient "P." Transmitter mat 856 generates an electromagnetic field around at least a portion of the patient "P" within which the position of a plurality of reference sensors 854 and the sensor 844 can be determined with use of a tracking module 852. One or more of reference sensors 854 are attached to the chest of the patient "P." The six degrees of freedom coordinates of reference sensors 854 are sent to computing device 825 (which includes the appropriate software) where they are used to calculate a patient coordinate frame of reference. Registration, is generally performed to coordinate locations of the three-dimensional model and two-dimensional images from the planning phase with the patient's "P's" airways as observed through the bronchoscope 830, and allow for the navigation phase to be undertaken with precise knowledge of the location of the sensor 844, even in portions of the airway where the bronchoscope 830 cannot reach. Further details of such a registration technique and their implementation in luminal navigation can be found in U.S. Patent Application Pub. No. 2011/0085720, the entire content of which is incorporated herein by reference, although other suitable techniques are also contemplated.

Registration of the patient's "P's" location on the transmitter mat 856 is performed by moving LG 832 through the airways of the patient's "P." More specifically, data pertaining to locations of sensor 844, while locatable guide 832 is moving through the airways, is recorded using transmitter mat 856, reference sensors 854, and tracking module 852. A shape resulting from this location data is compared to an interior geometry of passages of the three dimensional model generated in the planning phase, and a location correlation between the shape and the three dimensional model based on the comparison is determined, e.g., utilizing the software on computing device 825. In addition, the software identifies non-tissue space (e.g., air filled cavities) in the three-dimensional model. The software aligns, or registers, an image representing a location of sensor 844 with the three-dimensional model and two-dimensional images generated from the three-dimension model, which are based on the recorded location data and an assumption that locatable guide 832 remains located in non-tissue space in the patient's "P's" airways. Alternatively, a manual registration technique may be employed by navigating the bronchoscope 830 with the sensor 844 to pre-specified locations in the lungs of the patient "P", and manually correlating the images from the bronchoscope to the model data of the three dimensional model.

Following registration of the patient "P" to the image data and pathway plan, a user interface is displayed in the navigation software which sets for the pathway that the clinician is to follow to reach the target. One such navigation software is the ILOGIC® navigation suite currently sold by Medtronic PLC.

Once EWC 812 has been successfully navigated proximate the target as depicted on the user interface, the locatable guide 832 may be unlocked from EWC 812 and removed, leaving EWC 812 in place as a guide channel for guiding medical devices including without limitation, optical systems, ultrasound probes, marker placement tools, biopsy tools, ablation tools (i.e., microwave ablation devices), laser probes, cryogenic probes, sensor probes, and aspirating needles to the target.

The disclosed exemplary system 800 may be employed by the method of FIG. 7 to construct fluoroscopic-based three-dimensional volumetric data of a target located in the lungs area and to correct the location of a medical device navigated to the target area with respect to the target.

System 800 or similar version of it in conjunction with the method of FIG. 7 may be used in various procedures, other than ENB procedures with the required modifications, and such as laparoscopy or robotic-assisted surgery.

Systems and methods in accordance with the disclosure may be usable for facilitating the navigation of a medical device to a target and/or its area using real-time two-dimensional fluoroscopic images of the target area. The navigation is facilitated by using local three-dimensional volumetric data, in which small soft-tissue objects are visible, constructed from a sequence of fluoroscopic images captured by a standard fluoroscopic imaging device available in most procedure rooms. The fluoroscopic-based constructed local three-dimensional volumetric data may be used to correct a location of a medical device with respect to a target or may be locally registered with previously acquired volumetric data (e.g., CT data). In general, the location of the medical device may be determined by a tracking system, for example, an electromagnetic tracking system. The tracking system may be registered with the previously acquired volumetric data. A local registration of the real-time three-dimensional fluoroscopic data to the previously acquired volumetric data may be then performed via the tracking system. Such real-time data, may be used, for example, for guidance, navigation planning, improved navigation accuracy, navigation confirmation, and treatment confirmation.

In some embodiments, the methods disclosed may further include a step for generating a 3D rendering of the target area based on a pre-operative CT scan. A display of the target area may then include a display of the 3D rendering. In another step, the tracking system may be registered with the 3D rendering. As described above, a correction of the location of the medical device with respect to the target, based on the determined offset, may then include the local updating of the registration between the tracking system and the 3D rendering in the target area. In some embodiments, the methods disclosed may further include a step for registering the fluoroscopic 3D reconstruction to the tracking system. In another step, and based on the above, a local registration between the fluoroscopic 3D reconstruction and the 3D rendering may be performed in the target area.

From the foregoing and with reference to the various figure drawings, those skilled in the art will appreciate that certain modifications can also be made to the disclosure without departing from the scope of the same. For example, although the systems and methods are described as usable with an EMN system for navigation through a luminal network such as the lungs, the systems and methods described herein may be utilized with systems that utilize other navigation and treatment devices such as percutaneous devices. Additionally, although the above-described system and method is described as used within a patient's luminal network, it is appreciated that the above-described systems and methods may be utilized in other target regions such as the liver. Further, the above-described systems and methods are also usable for transthoracic needle aspiration procedures.

Detailed embodiments of the disclosure are disclosed herein. However, the disclosed embodiments are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ the disclosure in virtually any appropriately detailed structure.

As can be appreciated a medical instrument such as a biopsy tool or an energy device, such as a microwave ablation catheter, that is positionable through one or more branched luminal networks of a patient to treat tissue may prove useful in the surgical arena and the disclosure is directed to systems and methods that are usable with such instruments and tools. Access to luminal networks may be percutaneous or through natural orifice using navigation techniques. Additionally, navigation through a luminal network may be accomplished using image-guidance. These image-guidance systems may be separate or integrated with the energy device or a separate access tool and may include MRI, CT, fluoroscopy, ultrasound, electrical impedance tomography, optical, and/or device tracking systems. Methodologies for locating the access tool include EM, IR, echolocation, optical, and others. Tracking systems may be integrated to an imaging device, where tracking is done in virtual space or fused with preoperative or live images. In some cases the treatment target may be directly accessed from within the lumen, such as for the treatment of the endobronchial wall for COPD, Asthma, lung cancer, etc. In other cases, the energy device and/or an additional access tool may be required to pierce the lumen and extend into other tissues to reach the target, such as for the treatment of disease within the parenchyma. Final localization and confirmation of energy device or tool placement may be performed with imaging and/or navigational guidance using a standard fluoroscopic imaging device incorporated with methods and systems described above.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for estimating a pose of an imaging device, the method comprising:
    generating a probability map based on a captured image of a structure of markers captured by the imaging device;

generating candidates for a possible image of the structure of markers captured by the imaging device corresponding to possible poses of the imaging device, yielding generated candidates;

identifying a candidate from the generated candidates having the highest probability of being the captured image of the structure of markers based on the probability map, yielding an identified candidate; and estimating the pose of the imaging device for the captured image based on a possible pose of the imaging device corresponding to the identified candidate, yielding an estimated pose.

2. The method of claim 1, further comprising:

generating a locally deformed version of the identified candidate to maximize its probability of being the captured image of the structure of markers based on the probability map;

determining an improved candidate for the captured image of the structure of markers based on the locally deformed version of the identified candidate; and determining the possible pose of the imaging device associated with the improved candidate as the estimated pose of the imaging device for the captured image.

3. The method of claim 2, further comprising repeating: generating a locally deformed version of the identified candidate and determining an improved candidate.

4. The method of claim 1, wherein generating a probability map includes generating an image of smooth densities based on the captured image.

5. The method of claim 4, wherein the image of smooth densities includes pixels indicating a probability that the pixels show a portion of the structure of markers.

6. The method of claim 4, wherein the image of smooth densities is generated using a Harris corner detector.

7. The method of claim 1, wherein markers of the structure of markers are arranged in a periodic pattern.

8. The method of claim 1, further comprising:

capturing a sequence of images;

determining non-sequential images of the sequence of images;

estimating the pose of the imaging device for the non-sequential images;

reducing a range of possible poses for the imaging device based on the estimated poses of the imaging device for the non-sequential images, yielding a reduced range; and estimating the pose of the imaging device for images of the sequence of images other than the non-sequential images according to the reduced range.

9. A system for estimating a pose of an imaging device for an image acquired by the imaging device, the system comprising:

a structure of markers;

an imaging device configured to acquire an image of at least a portion of the structure of markers;

at least one processor; and a memory having stored thereon instructions, which, when executed by the at least one processor, causes the at least one processor to:

generate a probability map based on a captured image of a structure of markers captured by the imaging device;

generate candidates for possible images of the structure of markers captured by the imaging device at different possible poses, yielding generated candidates; and identify a candidate from the generated candidates having the highest probability of being the captured image of the structure of markers based on the probability map, yielding an identified candidate.

10. The system of claim 9, wherein the instructions, when executed by the at least one processor, further cause the at least one processor to:

generate a locally deformed version of the identified candidate to locally maximize the identified candidate's probability of being the captured image of the structure of markers based on the probability map; and determine an improved candidate for the captured image of the structure of markers based on the locally deformed version of the identified candidate.

11. The system of claim 9, wherein each marker of the structure of markers is a radio-opaque sphere.

12. The system of claim 9, wherein markers of the structure of markers are arranged in aurid pattern.

13. The system of claim 9, wherein the imaging device is a fluoroscopic imaging device.

14. The system of claim 9, wherein generating a probability map includes generating an image of smooth densities using a marker detector.

15. A system for estimating poses for a sequence of images, the system comprising:

at least one processor; and a memory having stored thereon instructions, which, when executed by the at least one processor, causes the at least one processor to:

generate probability maps based on a sequence of images of a structure of markers;

generate, for each image of the sequence of images, candidates for possible images of the structure of markers at different possible poses of an imaging device, yielding generated candidates; and identify, for each image of the sequence of images, a candidate from the generated candidates having the highest probability of being the image of the structure of markers based on the probability map for the image, yielding identified candidates.

16. The system of claim 15, wherein the instructions, when executed by the at least one processor, further cause the at least one processor to:

generate locally deformed versions of the identified candidates to locally maximize their probability of being the sequence of images of the structure of markers based on the probability maps; and determine improved candidates for possible images of the structure of markers based on the locally deformed versions of the identified candidates.

17. The system of claim 15, wherein markers of the structure of markers are radio-opaque spheres.

18. The system of claim 15, wherein markers of the structure of markers are arranged in a grid pattern.

19. The system of claim 15, wherein the instructions, when executed by the at least one processor, further cause the at least one processor to:

determine non-sequential images of the sequence of images;

estimate poses for the non-sequential images, yielding estimated poses for the non-sequential images;

reduce a range of the different possible poses based on the estimated poses for the non-sequential images, yielding a reduced range; and estimate poses for images of the sequence of images other than the non-sequential images according to the reduced range.

20. The system of claim 15, wherein markers of the structure of markers are arranged in a two-dimensional pattern.

* * * * *